US008728735B2

(12) United States Patent
Denomme

(10) Patent No.: US 8,728,735 B2
(45) Date of Patent: May 20, 2014

(54) METHOD FOR THE SIMULTANEOUS DETERMINATION OF BLOOD GROUP AND PLATELET ANTIGEN GENOTYPES

(75) Inventor: Gregory A Denomme, Hamilton (CA)

(73) Assignee: Canadian Blood Services, Ottawa, Ontario (CA)

( * ) Notice: Subject to any disclaimer, the term of this patent is extended or adjusted under 35 U.S.C. 154(b) by 0 days.

(21) Appl. No.: 12/551,881

(22) Filed: Sep. 1, 2009

(65) Prior Publication Data

US 2010/0112574 A1    May 6, 2010

Related U.S. Application Data

(63) Continuation of application No. 10/588,631, filed as application No. PCT/CA2005/000250 on Feb. 7, 2005, now abandoned.

(60) Provisional application No. 60/541,932, filed on Feb. 6, 2004.

(51) Int. Cl.
  C12Q 1/68    (2006.01)
  C12P 19/34   (2006.01)
  C07H 21/04   (2006.01)

(52) U.S. Cl.
  USPC ........ 435/6.12; 435/6.1; 435/6.11; 536/24.33

(58) Field of Classification Search
  None
  See application file for complete search history.

(56) References Cited

U.S. PATENT DOCUMENTS

| 5,804,379 | A | 9/1998 | Lee |
| 5,972,602 | A | 10/1999 | Hyland et al. |
| 6,287,778 | B1 * | 9/2001 | Huang et al. ............. 506/4 |
| 7,157,564 | B1 * | 1/2007 | Mittmann et al. ......... 536/23.1 |

FOREIGN PATENT DOCUMENTS

| DE | 10049363 A1 | 10/2001 |
| WO | 96/15268 A1 | 5/1996 |
| WO | 00/20634 | 4/2000 |
| WO | 01/32702 | 5/2001 |
| WO | 02/30950 | 4/2002 |
| WO | 02/068684 | 9/2002 |

OTHER PUBLICATIONS

Singer-Sam et al., "A Sensitive, Quantitative Assay for Measurement of Allele-specific Transcripts Differing by a Single Nucleotide," Genome Research, 1992, vol. 1, pp. 160-163.*
Chapela et al., "Molecular identification of cephalopod species by FINS and PCR-RFLP of a cytochrome b gene fragment," Eur. Food. Res. Technol., 2003, vol. 217, pp. 524-529.*
Okuda et al., "The Analysis of Nucleotide Substitutions, Gaps, and Recombination Events between RHD and RHCE Genes through Complete Sequencing," Biochemical and Biophysical Research Communications 274:670-683, 2000.
Bufflier, et al., "Development of a new DNA Chip System for Blood Platelet Genotype Characterization." Transfusion, 43:92 (2003).
Database Geneseq [Online], Jan. 22, 2002, "Human RhD exon 4 PCR primer PRHE41R." XP002469118, retrieved from EBI accession No. GSN:AAI68778. Database accession No. AAi68778.
Denomme, G.A. and Van Oene, M., "High-Throughput Multiplex Single-Nucleotide Polymorphism Analysis for Red Cell and Platelet Antigen Genotypes," Transfusion, 45:660-666 (2005).
Lee, C.: "SNP included in the dbSNP of NCBI under the entry corresponding to RefSNP rs1053352." Database SNP (NCBI) [Online], Sep. 13, 2000; XP002469116. Database accession No. ss1530464, abstract.
Maaskant-Van Wijk, P.A. et al., "Genotyping or RhD by Multiplex Polymerase Chain Reactions Analysis of Six RhD-Specific Exons." Transfusion, American Association of Blood Banks, 11(38):1015-1021 (1998).
Ouwehand, W. et al, "A Tyrosine703 Serine Polymorphism of CD109 Defines the Gov Platelet Alloantigens," Blood, 98(11), part 1:443a (2001).
Petrik, J., "Microarray Technology: The Future of Blood Testing?" Vox Sanguinis, 80:1-11 (2001).
Bortolin, et al.., "Analytical Validation of the Tag-It High-Throughput Microsphere-Based Universal Array Genotyping Platform: Application to the Multiplex Detection of a Panel of Thrombophilia-Associated Single-Nucleotide Polymorphisms," Clinical Chemistry, vol. 50; No. 11: pp. 2028-2036 (2004).
Gassner, et al., "RHD/CE typing by polymerase chain reaction using sequence-specific primers," Transfusion, vol. 37: pp. 1020-1026, (1997).
Hirschhorn, et al., "SBE-TAGS: An array-based method for efficient single-nucleotide polymorphism genotyping," PNAS, vol. 97; No. 22: pp. 12164-12169, (2000).
Inagaki, et al., "A new 39-plex analysis method for SNPs including 15 blood group loci," Forensic Science International, vol. 144: pp. 45-57, (2004).
Lee, S. et al. Point Mutations Characterize KEL10, the KEL3, KEL4, and KEL21 Alleles, and the KEL17 and KEL11 Alleles, Transfusion, Jan. 1, 1996, vol. 36, No. 6, pp. 490-494.
St. Louis, M. et al., Extended blood grouping of blood donors using automatable PCR-ELISA genotyping, Transfusion, Aug. 1, 2003, vol. 43, No. 8, pp. 1126-1132.
Lee S., Molecular basis of Kell blood group phenotypes, VoxSanguinis, 1997, vol. 73, No. 1, pp. 1-11.
van der Schoot, C.E. et al, Prenatal typing of Rh and kell blood group system antigens: The edge of a watershed, Transfusion, Jan. 1, 2003, vol. 17, No. 1, pp. 31-44.

(Continued)

*Primary Examiner* — Young J Kim
(74) *Attorney, Agent, or Firm* — Nixon Peabody LLP; David S. Resnick; Leena H. Karttunen Contarino

(57) ABSTRACT

RBC and platelet (Plt) alloimmunization requires antigen-matched blood to avoid adverse transfusion reactions. Some blood collection facilities use unregulated Abs to reduce the cost of mass screening, and later confirm the phenotype with government approved reagents. Alternatively, RBC and Plt antigens can be screened by virtue of their associated single nucleotide polymorphisms (SNPs). We developed a multiplex PCR-oligonucleotide extension assay using the GenomeLab SNPStream platform to genotype blood for a plurality of blood group antigen-associated SNPs, including but not limited to: RhD (2), RhC/c, RhE/e, S/s, K/k, $Kp^{a/b}$, Fya/b, FY0, $Jk^{a/b}$, $Di^{a/b}$, and HPA-1a/b.

9 Claims, 15 Drawing Sheets

(56) References Cited

OTHER PUBLICATIONS

Petrik J.,Microarray technology: the future of blood testing?, VoxSanguinis, Jan. 1, 2001, vol. 80, No. 1, pp. 1-11.
Graf S. et al. Genotyping of HPA-1 by mini-sequencing. Blood, Nov. 16, 2000; 96(11): 53b. Abstract only.
European Search Report issued in EP application No. 10011108.7 on Feb. 22, 2011.
Wagner et al., GenBank, Accession No. AJ287297, first seen at NCBI on Feb. 21, 2000.
Schuh, et al, "A tyrosine703serine polymorphism of CD109 defines the Gov platelet alloantigens", Blood, vol. 99, pp. 1692-1698, 2002.

* cited by examiner

| HPA-1a/b | 1 | 2 | 3 | 4 | 5 | 6 | 7 | 8* | 9 | 10 | 11 | 12 | 13 |
|---|---|---|---|---|---|---|---|---|---|---|---|---|---|
| UHT | a/a | a/b | a/b | a/b | a/b | a/b | a/b | b/b | b/b | b/b | b/b | a/a | a/a |
| PCR-RFLP | a/a | a/b | a/b | a/b | a/b | a/b | a/b | b/b | b/b | b/b | b/b | a/a | a/a |

| JKA/B | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| UHT | a/b | b/b | b/b | b/b | b/b | b/b | a/b | a/b | a/b | a/b | a/b | a/b | a/a | a/a |
| PCR-RFLP | a/b | b/b | b/b | b/b | b/b | b/b | a/b | a/b | a/b | a/b | a/b | a/b | a/a | a/a |

Current spot: (2.3) SNP: CBS_RHD4_TC at Segment 1 of plate: 1457302
Total:380  XX:64=○--  XY:293=□----  YY:0=⊕----  NEG:8=●
           Org Fail:0=△  Geno Fail:4=◆  QC Fail:0=▼--  Empty:11=☆
           Call Rate: 357/372=95.97

Current spot: (2.2) SNP: CBS_FEL6_TC at Segment 1 of plate: 1457302
Total:380   XX:0=∘ – –   XY:28=▫ – – –   YY:326=• – – –   NEG:8=•
Org Fail:0=△   Geno Fail:4=♦   QC Fail:0=▾ – – Empty:14=☆
Call Rate: 354/372=95.16

Current spot: (4.3) SNP: CBS_FEL8_TC at Segment 1 of plate: 1457302
Total:380   XX:0=∘ --   XY:1=□ ---   YY:354=• ---   NEG:8=•
Org Fail:0=△   Geno Fail:8=♦   QC Fail:1=▼ --   Empty:8=☆
Call Rate: 355/372=95.43

SEQUENCE LISTING

<160> NUMBER OF SEQ ID NOS: 37

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 1
agacaaactg ggtatcgttg c                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
atctacgtgt tcgcagcct                                                 19

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
ccaaaccttt taacattaaa ttatgc                                         26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
ttggtcatca aaatatttag cctc                                           24

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
tgtgcagtgg gcaatcct                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6

```
ccaccatccc aatacctg                                               18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 7
aaccaccctc tctggccc                                               18

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
atagtaggtg ttgaacatgg cat                                         23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
acatgtcttt cttatttgga cttac                                       25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
tttgtcaaat attaacatac ctggtac                                     27

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
tctctctcct ttaaagcttg ga                                          22

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
agaggcagga tgaggtcc                                               18
```

-continued

```
<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
agcaaggtgc aagaacact                                                 19

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
agagcttgcc ctgtgccc                                                  18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
tgtccctgcc cagaacct                                                  18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16
agacagaagg gctgggac                                                  18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 17
agtgcagagt catccagca                                                 19

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 18
ttcgaagatg tatggaattc ttc                                            23

<210> SEQ ID NO 19
```

```
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 19
catgaacatt cctcccattg                                                   20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 20
tttagtcctg agttctgacc cc                                                22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 21
atccagatca tctgcctgg                                                    19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 22
cggcacagtg aggatgag                                                     18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 23
attctggggc acagttatcc                                                   20

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 24
atagttctga ttgctggact tctc                                              24

<210> SEQ ID NO 25
<211> LENGTH: 45
<212> TYPE: DNA
```

<213> ORGANISM: Artificial Sequence
<220> FEATURE:
<223> OTHER INFORMATION: Description of Artificial Sequence: 5' tagged
      extension primer

<400> SEQUENCE: 25
gtgattctgt acgtgtcgcc gtctgatctt tatcctccgt tccct                45

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 26
gcggtaggtt cccgacatat tttaaacagg tttgctccta aatct                45

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 27
ggatggcgtt ccgtcctatt ggacggcttc ctgagccagt tccct                45

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 28
cgactgtagg tgcgtaactc gatgttctgg ccaagtgtca actct                45

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 29
agggtctcta cgctgacgat ttgaaatttt gctttatagg agaaa                45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 30
agcgatctgc gagaccgtat tggacttcct taaactttaa ccgaa                45

<210> SEQ ID NO 31
<211> LENGTH: 45
<212> TYPE: DNA
<213> ORGANISM: Artificial Sequence
<220> FEATURE:

<223> OTHER INFORMATION: Description of Artificial Sequence: 5' tagged
      extension primer

<400> SEQUENCE: 31
agatagagtc gatgccagct ttccttgtca atctccatca cttca                45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 32
gacctgggtg tcgataccta ggccctcatt agtccttggc tctta                45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 33
acgcacgtcc acggtgattt gggggcagct gcttccaggt tggca                45

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 34
cgtgccgctc gtgatagaat aaacccccaga gtccaaagta gatgt              45

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 35
ggctatgatt cgcaatgctt gtgctgtggg tggtgaagtc cacgc                45

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: 5' tagged
      extension primer

<400> SEQUENCE: 36
agagcgagtg acgcatactt gggctcctgt cttaca                          36

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: 5' tagged
      extension primer

```
<400> SEQUENCE: 37
gccctgcctc                                                                                      10
```

METHOD FOR THE SIMULTANEOUS DETERMINATION OF BLOOD GROUP AND PLATELET ANTIGEN GENOTYPES

CROSS-REFERENCE TO RELATED APPLICATIONS

The present application is a Continuation of U.S. Utility application Ser. No. 10/588,631, which is a 371 National Stage of International Application No. PCT/CA2005/000250 filed on Feb. 7, 2005, which designated the U.S., and which claims benefit under 35 U.S.C. §119(e) of the U.S. provisional application Ser. No. 60/541,932, filed Feb. 6, 2004.

TECHNICAL FIELD

This invention relates to an ultra high throughput (UHT) multiplex PCR genotyping method. More specifically, the present invention relates to an automated method of determining a plurality of blood group and platelet antigen, preferably human platelet antigen (HPA), genotypes simultaneously from a single sample through the detection of single nucleotide polymorphisms (SNPs) for various blood group and platelet antigens.

BACKGROUND OF THE INVENTION

At present, there are 29 blood group systems and 6 HPA systems recognized by the International Society of Blood Transfusion (ISBT), wherein, with a few exceptions, a blood group 'system' may be defined by a single gene at a given locus of the human genome (Daniels, G. L. et al. Vox Sang 2003; 84:244; Metcalfe P. et al., Vox Sang. 2003; 85:240). Most people know their ABO and Rh blood group. However, the ABO and Rh blood group systems expressed on red cells simply represent antigens from only two of the 29 blood group systems, and more systems are being discovered each year. Some examples of blood group systems are the ABO, Rh (D, C, c, E, e), P, Lutheran, Kell (K, k), Lewis, Duffy ($Fy^a$, $Fy^b$), or Kidd ($Jk^a$, $Jk^b$). Moreover, there are over 250 blood group and 12 human platelet antigens assigned to one of the blood group or HPA systems, respectively. A system is defined by a gene or group of genes at a specific locus of the human genome. The alleles or genotype of a person for each blood group or HPA system represent the unique nucleotide gene sequences that express specific blood group or platelet antigens (for a review see Denomme, G. et al., Approaches to Blood Group Molecular Genotyping and Its Applications: in Stowell, C. and Dzik W., editors; *Emerging Technologies in Transfusion Medicine*, AABB 2003, Ch 4).

A blood group or HPA system maps to a specific region of the human genome, termed a locus. Nearly all blood group or HPAs can be identified by the presence of its unique nucleotide sequence, termed an 'allele', at the locus of interest. Every person has two alleles for any given autosomal gene. Some individuals are homozygotes for a specific allele, i.e. they have two identical alleles, while others are heterozygotes for a specific allele, i.e. they have two different alleles. By definition, alleles that represent different blood group or HPAs differ by at least one nucleotide; sometimes they differ by several nucleotides. For example, a deoxythymidine (T) or a deoxycytidine (C) nucleotide can be found at cDNA position 196 of the glycoprotein IIIa (GP3A) gene that expresses the HPA-1 (Newman P. J. et al., J Clin Invest 1989; 83:1778). The allele containing the deoxthymidine nucleotide expresses the HPA-1a antigen and the allele containing the deoxycytidine nucleotide expresses the HPA-1b antigen. We refer to the T/C nucleotide difference between the two alleles as a single nucleotide polymorphism (SNP).

Blood group alleles for a given blood group system represent genetic variations of the same gene. For example, the ABO blood group system has 3 common alleles, that confer 6 genotypes within this blood group system. Moreover, many alleles within a blood group system express different blood group 'antigens', that is to say, dependent on the allelic genotype the corresponding antigenic phenotype is accordingly expressed. Alleles differ in their nucleotide sequence, and the difference between one allele and another, usually within a single blood group system, may be one single nucleotide variation. Therefore, two alleles can differ by one nucleotide, i.e. a SNP and represent a co-dominant bi-allelic system. Alternatively, alleles can differ by a few to several dispersed nucleotides, or by a stretch of nucleotides, any one of which can be used to identify the alleles. Regardless of whether the variations in the nucleotide are due to single or multiple nucleotide differences, the phenotype associated with a specific genotype (the specific nucleotide sequence) will result in the expression of a specific blood group or platelet antigen on the red cell or platelet surface, respectively.

Normally, all blood donations are blood grouped for ABO and RhD. However, sometimes a previously transfused recipient will require more blood that is antigen-matched with one of their own antigens because they have made antibodies to a different blood group or platelet antigen. The gold standard in the industry is to 'phenotype' blood for the presence of specific blood group and platelet antigens using government regulated antisera (antibodies) performed by single-test methods or by an automated platform, which is a cost ineffective method for a blood collection facility that routinely performs tests on a high volume basis.

Blood group phenotypes are presently determined using commercially available government-regulated serological reagents and human red cells. These known tests rely on the principle of antibody binding and red cell agglutination to identify clinically important blood group phenotypes. The presently known tests were originally devised some 60 years ago and today require the use of government regulated (for example, Health Canada) approved serological reagents. Some of the tests being employed today have been automated (for example, ABO and Rh typing) while some have been semi-automated (for example, RhC/c and RhE/e). However, many of the presently used tests are performed manually by highly-trained laboratory technologists and are done on a test-by-test basis. In other words, a technologist must perform four separate tests to determine, for example, the $Fy^a$, $Fy^b$, $Jk^a$ and $Jk^b$ phenotype of a single blood donation. Essentially, the current tests which employ government-approved reagents in a manual, single-test driven method are a very cost ineffective method for a blood collection facility that is often required to perform such tests on a high volume basis.

In an effort to reduce costs, a blood collection facility will often use non-regulated antisera to 'screen' blood donations for important blood group phenotypes and then confirm the phenotype with the regulated antisera. However, since much of the blood is sent to hospitals within 24-48 hours after collection, manual blood group phenotyping cannot meet the short turn-around time required to provide the end user with the information required before blood must be shipped. Therefore, hospital blood banks must perform their own tests on the blood that they have in their inventories. It would be advantageous to provide a cost effective blood screening method that would provide quick and reliable results relating to the clinically important blood group phenotypes.

The prior art uses two basic techniques to detect SNPs; polymerase chain reaction-restriction fragment length polymorphism (PCR-RFLP)(Chaudhuri A., et al. 1995; 85:615), and sequence specific primer (SSP)-PCR (McFarland J. G. et al., Blood 1991; 78:2276). For PCR-RFLP analysis, restriction enzymes are used to digest PCR amplified genomic DNA fragments. In brief, DNA is extracted from nucleated blood cells manually for each blood sample to be analyzed. The PCR is set up manually; a separate PCR is performed on each sample for each SNP of interest. The PCR amplified fragments are digested with a specific restriction enzyme and the digested products are separated on a gel. The pattern of digested DNA fragments viewed from the gel predicts the presence or absence of either nucleotide of a SNP of interest. In SSP-PCR, two PCRs are set up in separate tubes for each SNP of interest. One tube contains a universal primer and a primer with a sequence that is specific to detect one nucleotide of a SNP. The other tube contains the same universal primer and a primer specific for the other nucleotide of a SNP. Prior art has used two pair or three pair PCR to analyze a nucleotide for a given SNP, with at least one pair acting as an internal control to ensure DNA is available for PCR amplification. The prior art does not provide the use of multiple DNA sequences as primer pairs that work simultaneously on a single sample. Moreover, the prior art does not employ novel DNA sequences to detect blood group SNPs in an automated high-throughput fashion.

St-Louis M., et al. (*Transfusion* 2003; 43:11126-32) have used allele-specific PCR-ELISA to detect blood group SNPs, wherein some of the PCR primers were publicly known and all primers were labeled with digoxigenin; SNPs were detected by oligonucleotide hybridization using solid-phase microplate wells coated with individual blood group-specific complementary oligonucleotides. An abstract by Buffleir E. et al. (*Transfusion* 2003; 43:92A) outlines a combined HPA-1 and HPA-5 genotyping method that uses biotin labeled PCR-amplified targets and allele specific oligonucleotide probes arrayed on the bottom of 96 well microplates. Specific hybridization is detected with the use of an enzyme conjugate which produces a specific colourimetric signal. An array of several oligonucleotides reportedly can be used to detect HPA SNPs. The publications, cited above, do not use multiplex PCR primers, nor do they use extension probes, and rely on a less sensitive and more error-prone allele-specific hybridization to detect the SNPs. There are a few other publications that refer to the multiplex PCR amplification of the RHD gene alone, or together with sex determination, or with internal control primers designed to confirm the presence of DNA in various blood group PCR applications. U.S. Pat. No. 5,723, 293 describes a diagnostic method and kit for determining Rh blood group genotypes, wherein there is provided a method for directly determining D and associated CcEe genotypes using restriction fragment length polymorphisms (RFLPs) for diagnosis. U.S. Pat. No. 5,804,379 describes a diagnostic method and kit for determining Kell blood group genotype, wherein there is provided a method for determining the K1/K2 genotype using RFLPs for diagnosis. U.S. Pat. No. 5,780,229 provides polynucleotides for determining the Pen polymorphism of human platelet membrane glycoprotein Ma, and generally describes diagnostic and therapeutic uses relating to the "Pen" human platelet polymorphism (HPA-4) and differs from the teachings of the present invention. United States patent application 20020098528 describes methods and apparatus for blood typing with optical bio-disc, and essentially describes a method for determining the ABO blood cell type of an individual with optical bio-discs and a disc-reading apparatus.

In the SSP-PCR application by St. Louis et al. (*Transfusion* 2003; 43:1126), two PCR primer pairs are set up, each in a separate well, to detect the nucleotides of a SNP of interest. For example, one primer pair containing a universal primer and a sequence specific primer is set up in a tube to detect a nucleotide of a SNP. Another primer pair containing the same universal and another sequence specific primer is set up in another tube to detect the alternate nucleotide for the same SNP. In addition, each tube includes a primer pair that detects a universal sequence contained in all human DNA. Contained in the PCR tube is digoxigenin-dUTP that is incorporated into the amplified DNA fragment if the sequence specific primer detects the appropriate nucleotide of an SNP. For the detection phase, one of each primer pair contains the chemical tag biotin, which is used to capture the DNA amplified fragment in sets of microtitre wells containing streptavidin. An optical colorimetric assay is used to detect the presence of digoxigenin-dUTP in each of the wells; anti-digoxigenin peroxidase conjugated antibody detects the presence of digoxigenin dUTP and the peroxidase can convert a substrate added to the well into a colored end product. Therefore, the presence of a nucleotide of a SNP is detected by the presence of a color in the microtitre well. Such assays are routinely designed in a 96-well microtitre plate format to facilitate semi-automation. The colorimetric results are evaluated by the operator to determine the presence or absence of the nucleotides for a SNP. The deficiencies of these test systems are the use of a single PCR reaction for each nucleotide of a given nucleotide of each SNP, and the pooling of samples prior to the detection phase and manual post-analyte data analysis.

No prior art has used a multiple, or 12, primer pair multiplexed PCR that successfully works in a single tube, nor has prior art employed novel DNA sequences as probes to detect both nucleotides of a plurality of blood group and HPA genotypes simultaneously, such as the detection of all 12 blood group and HPA SNPs in these mixtures using an automated high-throughput platform.

Accordingly, there is a need for a high-throughput automated multiple blood-group associated SNP analysis of genomic DNA that is capable of rapidly and accurately determining the genotypes and associated phenotypes of a plurality of blood group systems in a single test sample.

SUMMARY OF THE INVENTION

The present invention provides a method of detecting the presence or absence of nucleotides relating to various SNPs for the determination of a specific genotype and accordingly the inferred phenotype. More specifically, the present invention allows for the detection of the presence or absence of two nucleotides of a plurality of different SNPs, and more preferably of the 12 SNPs in a preferred embodiment of the present invention.

The present invention accordingly provides an automated, or robotic, high-throughput 'screening' tool for blood group and platelet antigens by evaluating the alleles of the genes that express these antigens on red cells and platelets, respectively. This is done by identifying the unique nucleotides associated with the specific alleles that occupy the gene locus using a testing platform, which requires novel and specific compounds that we designed. Our robotic high-throughput platform provides important blood group and HPA genotype information within 24 hours from the start of the test. We identified the alleles of blood group antigens for; RhD, RhC, Rhc, RhE, Rhe, S, s, Duffy $(Fy)^a$, $Fy^b$, K, k, $Kp^a$, $Kp^b$, Diego $(Di)^a$, $Di^b$, Kidd $(Jk)^a$, $Jk^b$, and the platelet antigens, Human Platelet Antigen (HPA)-1a and HPA-1b, representing, but not limited to 19 of the most clinically important antigens in red cell and platelet transfusion. Additional genotyping tests for other clinically important blood group and platelet antigens may be developed, and are encompassed in the teachings of the present invention. When performed on all blood donations for all clinically important blood group and platelet antigens, our invention will provide a comprehensive database to select and confirm the antigens when required using government regulated antisera. The use of this platform as a screening tool will lessen the number of costly government regulated tests to be done by the collection facility and end user (the hospital blood bank), and meet the demand of antigen-matched blood for specific transfusion recipients.

The invention discloses a method for DNA-based blood group genotyping for clinically important blood group and platelet antigens. The technology uses an ultra high-throughput multiplex PCR design to detect specific SNPs that represent clinically important blood group antigens: RhD, RhC, Rhc, RhE, Rhe, S, s, Duffy (Fy)$^a$, Fy$^b$, K, k, Kp$^a$, Kp$^b$, Diego (Di)$^a$, Di$^b$, Kidd (Jk)$^a$, Jk$^b$, and the platelet antigens, Human Platelet Antigen (HPA)-1a and HPA-1b. It should be noted however that the present invention is not limited to the detection of SNPs for only the SNPs listed, but additionally comprises the detection of SNPs for all blood group and platelet antigens. The invention discloses novel DNA sequences of PCR primers that are specifically designed to avoid inter-primer pair cross-reactions and post-PCR probes that make multiple analyses possible. The invention represents a novel approach to screening multiple blood group and HPA genotypes at once and addresses a clear need in the art for novel, rapid, cost-effective and reliable genotyping. This additionally replaces the use of expensive and difficult-to-obtain serological reagents, which can be reserved for use to confirm only the donors identified by the screening process.

More specifically, the present invention analyzes the HPA-1 GP3A mutation incorporated into our SNP assay, and the other blood group antigen SNPs in a method according to the present invention.

The invention addresses the need for an automated, accurate, rapid and cost-effective approach to the identification of multiple blood group antigens. The multiplex SNP assay design and automated genotyping platform allows one trained research technician to identify a plurality of blood group alleles, and more specifically, 19 blood group alleles, overnight on 372 to 2232 individual blood samples. In one application of the present invention, the multiplex PCR and SNP detection platform analyzed the nucleotides of 12 SNPs overnight on 372 individual blood samples. The cost using current standard blood group serology for 372 samples is estimated at CDN$99,500, which reflects a reagent cost of CDN$54,000 (excluding new capital equipment investments) and an operator cost of CDN$45,500 to analyse each of the antigens by Gel Card technology (n=5), immediate spin tube test (n=2), indirect antiglobulin tube test (n=8), and platelet GTI® test (n=1). Approximate 10 to 15 fold cost savings are obtained in the simultaneous DNA-based determination of these blood group alleles. It should be noted that the present invention is not limited to the detection of only 12 SNPs, and may be optimally used for the detection a plurality of SNPs for potentially all blood group and platelet alleles. Accordingly, the products, methods, platform and teachings of the present invention can detect all blood group and HPA SNP variations on a great number of samples, such as 744 samples overnight, as further described below.

The present invention overcomes the deficiencies of the prior art because the entire test, i.e. all steps of the method of the present invention, from PCR to computation analyses can be automated and multiplexed so that the nucleotides of a plurality of SNPs, and more preferably, the 12 SNPs of the present invention, can be identified simultaneously. This automated multiplex high throughput analysis can meet the demand of testing hundreds of blood samples, and the turn-around time of less than 24 hours, to provide valuable information to a blood collection facility before blood is shipped to the end user. This platform has the advantage over existing technology in that it reduces operator handling error. In addition, there are significant cost reductions compared with the current government-regulated serological analysis. It should be noted that present prior art technologies relating to PCR-RFLP and SSP-PCR for blood group and platelet antigens are not routinely used since they are no more cost efficient than serology. The present invention overcomes the deficiencies of the prior art and fulfils an important need in the present art for the automated, accurate, rapid and cost-effective identification of multiple blood group and HPA SNPs.

The invention provides the opportunity to screen all blood donors to obtain a daily or 'live' repository of the genotypes or combinations of genotypes currently available for specific transfusion needs. Accordingly, the present invention fulfills a need relating to the collection and antigen screening of blood and blood products.

For convenience, some terms employed in the present specification are noted below. Unless defined otherwise, all technical and scientific terms used herein have the meanings commonly understood by one of ordinary skill in the present art.

The present invention provides a method or screening assay for the determination of blood genotypes of the various blood group and HPA systems through the ultra high throughput multiplex PCR analysis of SNPs in an automated platform (Petrick J. Vox Sang 2001; 80:1). A platform, as referred to herein, refers to a system of machine(s) and protocol(s) capable of analyzing multiplex PCR amplified SNPs, wherein said platform is not limited to, but may comprise the GenomeLab SNPStream (Beckman Coulter Inc., Fullerton, Calif.), the SNPSTREAM™ UHT (Orchid BioSciences, Princeton, N.J.), the SNPSTREAM™ 25K (Orchid BioSciences, Princeton, N.J.), the MALDI-TOF/Mass-Spectrophotometer Spectro CHIP (Sequenom, San Diego, Calif.), and the Gene Chip Microarray (Affymetrix, Inc., Santa Clara, Calif.), Nano Chip (Nanogen, San Diego, Calif.) and the Random Ordered Bead Arrays (Illumina, Inc., San Diego, Calif.) or any other system, machine or protocol capable of analyzing multiplex PCR amplified SNPs. Accordingly, the present invention provides a platform, or system and protocols, for the evaluation and detection of SNPs, for the purpose of typing (determining the genotype and corresponding phenotype) blood group and platelet, preferably, human platelet antigen (HPA) SNP analysis. A preferred platform that can be used in accordance with the present invention is the Orchid SNP-IT system for HLA typing (Orchid Bioscience, Princeton, N.J.), wherein a preferred embodiment of the present invention comprises the use of the primer pairs of Table 1 for the specific oligonucleotide primer extension of blood group and platelet, preferably, human platelet antigen (HPA) SNPs, and the probes of Table 2 for the specific hybridization thereof, and the simultaneous analysis of the absence or presence of a plurality of blood group and platelet, preferably, human platelet antigen (HPA) SNPs using a platform as described herein, or using any SNP analysis system capable of detecting multiplex PCR amplified SNPs.

For the purposes of the present disclosure, SNPs, may refer to any blood group and HPA SNPs, and more preferably refers to any of the SNPs specified in Table 1, or any other known blood group or HPA SNPs or single nucleotide changes including, but not limited to, nucleotide substitutions, deletions, insertions or inversions, that can be defined as a blood group or HPA SNP due to nucleotide differences at the specified position in a gene sequence.

Ultra high throughput (UHT) refers to the implementation of the platform in a rapid and optimized form, that is to say, through the analysis of multiple SNPs. That is to say, UHT analysis refers to the rapid and simultaneous evaluation of a plurality of samples for a plurality of markers, in this case SNPs. For example, the analysis of 12 SNPs (equivalent to 12 C and 12 T nucleotides) for 372 samples, would result in the generation of 8928 (i.e. 2×12×372) determinations that are analysed, an evaluation that far exceeds the number of evaluation points possible with manual or automated serological methods.

Phenotype in the context of red cell blood group and Human Platelet Antigen (HPA) refers to the expressed moiety of an allele for a given gene, and is also referred to in this document as 'antigen'. Genotype refers to the two alleles of an autosomal gene that occupy a given locus or alternatively to either one or two alleles of an X-linked gene that occupies a given locus.

Antigen refers to a red cell or platelet membrane carbohydrate, protein or glycoprotein that is expressed as a polymorphic structure among the human population, that is to say a moiety that is immunogenic in another animal, or human, due differences in its amino acid or carbohydrate composition. Blood group or red cell, or HPA or platelet antigen refers to a moiety expressed on red cells or platelets that has been assigned a blood group or Human Platelet Antigen (HPA) designation, or provisional or workshop designation. The present invention comprises a method and for the determination of the antigen genotype and corresponding phenotype of any blood group or red cell, or HPA or platelet antigen using multiplex PCR SNP analysis. The following two tables (Table A and Table B) list most of the known human blood group and platelet antigens. Many of the antigens can be identified by their unique nucleotide sequence.

TABLE A

Human Red Cell Blood Group Systems

| ISBT Name (ISBT Number) | Chromosome Location | Gene Name ISGN (ISBT) | Component Name (CD Number) | Associated Blood Group Antigens |
|---|---|---|---|---|
| ABO (001) | 9q34.2 | ABO (ABO) | Carbohydrate | A, B, A, B, A1 |
| MNS (002) | 4q28.2-q31.1 | GYPA (MNS) GYPB (MNS) | GPA (CD235a) GPB (CD235b) | M, N, Vw, S, s, U, He + 36 more |
| P (003) | 22q11.2-qter | P1 (P1) | Carbohydrate | P1 |
| Rh (004) | 1p36.13-p34.3 | RHD (RH) RHCE (RH) | RhD (CD240D) RhCE (CD240CE) | D, G, Tar C, E, c, e, V, Rh17 + 39 more |
| Lutheran (005) | 19q13.2 | LU (LU) | Lutheran glycoprotein B-CAM (CD239) | Lu$^a$, Lu$^b$, Lu3, Lu4, Au$^a$, Au$^b$ + 13 more |
| Kell (006) | 7q33 | KEL (KEL) | Kell glycoprotein (CD258) | K, k, Kp$^a$, Kp$^b$, Ku, Js$^a$, Js$^b$ + 17 more |
| Lewis (007) | 19p13.3 | FUT3 (LE) | Carbohydrate Adsorbed form plasma | Le$^a$, Le$^b$, Le$^{ab}$, Le$^{bh}$, ALe$^b$, BLe$^b$ |
| Duffy (008) | 1q22-q23 | DARC (FY) | Fy glycoprotein (CD234) | Fy$^a$, Fy$^b$, Fy3, Fy4, Fy5, Fy6 |
| Kidd (009) | 18q11-q12 | SLC14A1 (JK) | Kidd glycoprotein | Jk$^a$, Jk$^b$, Jk3 |
| Diego (010) | 17q21-q22 | SLC4A1 (DI) | Band 3, AE1 (CD233) | Di$^a$, Di$^b$, Wr$^a$, Wr$^b$, Wd$^a$, Rb$^a$ + 14 more |
| Yt (011) | 7q22 | ACHE (YT) | Acetylcholinesterase | Yt$^a$, Yt$^b$ |
| Xg (012) | Xp22.32 | XG (XG) MIC2 | Xg glycoprotein CD99 | Xg$^a$ CD99 |
| Scianna (013) | 1p34 | ERMAP (SC) | ERMAP | Sc1, Sc2, Sc3, Rd |
| Dombrock (014) | 12p13.2-p12.1 | DO (DO) | Do glycoprotein; ART 4 | Do$^a$, Do$^b$, Gy$^a$, Hy, Jo$^a$ |
| Colton (015) | 7p14 | AQP1 (CO) | Channel-forming integral protein | Co$^a$, Co$^b$, Co3 |
| Landsteiner-Wiener (016) | 19p13.3 | LW (LW) | LW glycoprotein (ICAM-4) (CD242) | LW$^a$, LW$^{ab}$, LW$^b$ |
| Chido/Rodgers (017) | 6p21.3 | C4B, C4A (CH/RG) | C4B, C4A | CH1, CH2, Rg1 + 6 more |
| Hh (018) | 19q13.3 | FUT1 (H) | Carbohydrate (CD173) | H |

TABLE A-continued

Human Red Cell Blood Group Systems

| ISBT Name (ISBT Number) | Chromosome Location | Gene Name ISGN (ISBT) | Component Name (CD Number) | Associated Blood Group Antigens |
|---|---|---|---|---|
| Kx (019) | Xp21.1 | XK (XK) | Xk glycoprotein | Kx |
| Gerbich (020) | 2q14-q21 | GYPC (GE) | GPC GPD (CD236) | Ge3, Ge4, Wb, $Ls^a$, $Dh^a$ Ge2, Ge3, $An^a$ |
| Cromer (021) | 1q32 | DAF (CROM) | DAF (CD55) | $Cr^a$, $Tc^a$, $Tc^b$, $Tc^c$, $Dr^a$, $Es^a$, IFC, $WES^a$, $WES^b$, UMC, GUTI |
| Knops (022) | 1q32 | CR1 (KN) | CR1 (CD35) | $Kn^a$, $Kn^b$, $McC^a$, $Sl^a$, $Yk^a$ |
| Indian (023) | 11p13 | CD44 (IN) | Hermes antigen (CD44) | $In^a$, $In^b$ |
| OK (024) | 19pter-p13.2 | CD147 (OK) | Neurothelin, basogin (CD147) | $Ok^a$ |
| RAPH (025) | 11p15.5 | MER2 (MER2) | Not defined | MER2 |
| JMH (026) | 15q22.3-q23 | SEMA-L (JMH) | H-Sema-L (CD108) | JMH |
| I (027) | 6p24 | CGNT2 (IGNT) | Carbohydrate | I |
| Globoside (028) | 3q25 | B3GALT3 (βGalNAcT1) | Carbohydrate ($Gb_4$, globoside) | P |
| GIL (029) | 9p13 | AQP3 (GIL) | AQP3 | GIL |

ISGN = International Society for Gene Nomenclature

TABLE B

Human Platelet Antigen Systems

| System | Gene Name | Chromosome Location | Component Name (CD) | Associated Antigens |
|---|---|---|---|---|
| HPA-1 | GP3A | 17q21.32 | Integrin β3 (CD61) | $Pl^{A1/2}$ |
| HPA-2 | GP1BA | 17pter-p12 | Glycoprotein Ibα (CD42b) | $Ko^{a/b}$ |
| HPA-3 | GP2B | 17q21.32 | Integrin α2b (CD41) | $Bak^{a/b}$ |
| HPA-4 | GP3A | 17q21.32 | Integrin β3 (CD61) | $Pen^{a/b}$ |
| HPA-5 | GP1A | 5q23-q31 | Integrin α2 (CD49b) | $Br^{a/b}$ |
| HPA-6w | GP3A | 17q21.32 | Integrin β3 (CD61) | $Ca^a/Tu^a$ |
| HPA-7w | GP3A | 17q21.32 | Integrin β3 (CD61) | $Mo^a$ |
| HPA-8w | GP3A | 17q21.32 | Integrin β3 (CD61) | $Sr^a$ |
| HPA-9w | GP2B | 17q21.32 | Integrin α2b (CD41) | $Max^a$ |
| HPA-10w | GP3A | 17q21.32 | Integrin β3 (CD61) | $La^a$ |
| HPA-11w | GP3A | 17q21.32 | Integrin β3 (CD61) | $Gro^a$ |
| HPA-12w | GP1BB | 22q11.2 | Glycoprotein Ibβ (CD42c) | $Ly^a$ |
| HPA-13w | GP1A | 5q23-q31 | Integrin α2 (CD49b) | $Sit^a$ |
| HPA-14w | GP3A | 17q21.32 | Integrin β3 (CD61) | $Oe^a$ |
| HPA-15 | AF410459 | 6q13 | GPI-linked GP (CD109) | $Gov^{a/b}$ |
| HPA-16w | GP3A | 17q21.32 | Integrin β3 (CD61) | $Duv^a$ |
| ? | GPV | ? | Glycoprotein V | $Pl^T$ |
| ? | GPIV | 7q11.2 | Glycoprotein IV (CD36) | $Vis^a/Nak^a$ |

Note:
HPA numbers on the left ending with a 'w' represent ISBT workshop designations and are tentative HPA systems.

A single nucleotide polymorphism (SNP) refers to any blood group or HPA allele that defines a specific red cell or platelet antigen by virtue of its unique nucleotide sequence as defined in Garratty et al. Transfusion 2000; 40:477 and as updated from time-to-time by the International Society of Blood Transfusion.

It is understood that the presently disclosed subject matter is not limited to the particular methodology, protocols, cell lines, vectors, and reagents described as these can vary. It is also to be understood that the terminology used herein is for the purpose of describing particular embodiments only, and is not intended to limit the scope of the presently disclosed subject matter.

Unless defined otherwise, all technical and scientific terms used herein are intended to have their meanings as understood by one skilled in the present art. Although any methods and materials similar or equivalent to those described herein can be used in the practice or testing of the presently disclosed subject matter, the preferred embodiments, methods, devices and materials described.

It is also understood that the articles 'a' and 'an' are used herein to refer to one or to more than one (i.e. to at least one) of the grammatical object of the article. Accordingly, 'an element' means one element or more than one element.

Our novel platform simultaneously performs automated multiple blood group-associated SNP analyses using genomic DNA and the *Thermus aquaticus* polymerase chain reaction (PCR) to infer the presence of specific blood group genotypes. This automated high-throughput platform has particular application in the blood donation industry since it represents a novel screening tool for the expression of blood group antigens or phenotypes.

Our platform provides important genotypic information within 24 hours of donation. When performed on all blood donations for all important blood group phenotypes, our invention will provide a comprehensive database to select and confirm blood group phenotypes using government regulated antisera. The use of this platform as a screening tool will lessen the number of regulated blood group phenotype tests done by the collection facility and end user, and meet the end user demand for antigen-matched blood for transfusion recipients.

Unique to this invention is the assay design for the simultaneous identification of a plurality of blood group or HPA alleles. The present invention provides novel assay for the simultaneous identification of a plurality of blood group or HPA alleles, and more preferably of 19 blood group alleles using a plurality of SNPs, and more preferably, 12 SNPs. In one embodiment, the genotyping platform queries genetic variants using multiplexed single nucleotide primer extension coupled with two-laser fluorescence detection and software for automated genotype calling. Each of the relevant gene regions are PCR amplified from purified genomic DNA in a single reaction using the following oligonucleotide primer designs:

| Gene | Primer | Sequence (5'- 3') |
|---|---|---|
| RHD Exon 4 | RHDe4S | AGACAAACTGGGTATCGTTGC (SEQ ID NO: 1) |
| | RHDe4A | ATCTACGTGTTCGCAGCCT (SEQ ID NO: 2) |
| RHD Exon 9 | RHDe9S | CCAAACCTTTTAACATTAAATTATGC (SEQ ID NO: 3) |
| | RHDe9A | TTGGTCATCAAAATATTTAGCCTC (SEQ ID NO: 4) |
| RHCE Exon 2 | RHCEe2S | TGTGCAGTGGGCAATCCT (SEQ ID NO: 5) |
| | RHCEe2A | CCACCATCCCAATACCTG (SEQ ID NO: 6) |
| RHCE Exon 5 | RHCEe5S | AACCACCCTCTCTGGCCC (SEQ ID NO: 7) |
| | RHCEe5A | ATAGTAGGTGTTGAACATGGCAT (SEQ ID NO: 8) |
| GYPB Exon 4 | GYPBe4S | ACATGTCTTTCTTATTTGGACTTAC (SEQ ID NO: 9) |
| | GYPBe4A | TTTGTCAAATATTAACATACCTGGTAC (SEQ ID NO: 10) |
| KEL Exon 6 | KELe6S | TCTCTCTCCTTTAAAGCTTGGA (SEQ ID NO: 11) |
| | KELe6A | AGAGGCAGGATGAGGTCC (SEQ ID NO: 12) |
| KEL Exon 8 | KELe8S | AGCAAGGTGCAAGAACACT (SEQ ID NO: 13) |
| | KELe8A | AGAGCTTGCCCTGTGCCC (SEQ ID NO: 14) |
| FY Promoter | FYproS | TGTCCCTGCCCAGAACCT (SEQ ID NO: 15) |
| | FYproA | AGACAGAAGGGCTGGGAC (SEQ ID NO: 16) |
| FY Exon 2 | FYe2S | AGTGCAGAGTCATCCAGCA (SEQ ID NO: 17) |
| | FYe2A | TTCGAAGATGTATGGAATTCTTC SEQ ID NO: 18) |
| JK Exon 9 | JKe9S | CATGAACATTCCTCCCATTG (SEQ ID NO: 19) |
| | JKe9A | TTTAGTCCTGAGTTCTGACCCC (SEQ ID NO: 20) |
| DI Exon 18 | DIe19S | ATCCAGATCATCTGCCTGG (SEQ ID NO: 21) |
| | DIe19A | CGGCACAGTGAGGATGAG (SEQ ID NO: 22) |
| GP3A | GP3Ae3S | ATTCTGGGGCACAGTTATCC (SEQ ID NO: 23) |
| | GP3Ae3A | ATAGTTCTGATTGCTGGACTTCTC (SEQ ID NO: 24) |

The above primer pairs comprise the corresponding forward and reverse primers, and may be referred to herein as SEQ ID NOs 1-24.

Multiplexed single nucleotide primer extension is performed using the following 5' tagged extension primers:

(SEQ ID NO: 25)
RHD Exon 4
GTGATTCTGTACGTGTCGCCGTCTGATCTTTATCCTCCGTTCCCT (SEQ ID NO: 26)
RHD Exon 9
GCGGTAGGTTCCCGACATATTTTAAACAGGTTTGCTCCTAAATCT (SEQ ID NO: 27)
RHCE Exon 2
GGATGGCGTTCCGTCCTATTGGACGGCTTCCTGAGCCAGTTCCCT (SEQ ID NO: 28)
RHCE Exon 5
CGACTGTAGGTGCGTAACTCGATGTTCTGGCCAAGTGTCAACTCT (SEQ ID NO: 29)
GYPB Exon 4
AGGGTCTCTACGCTGACGATTTGAAATTTTGCTTTATAGGAGAAA (SEQ ID NO: 30)
KEL Exon 6
AGCGATCTGCGAGACCGTATTGGACTTCCTTAAACTTTAACCGAA (SEQ ID NO: 31)
KEL Exon 8
AGATAGAGTCGATGCCAGCTTTCCTTGTCAATCTCCATCACTTCA (SEQ ID NO: 32)
FY Promoter
GACCTGGGTGTCGATACCTAGGCCCTCATTAGTCCTTGGCTCTTA (SEQ ID NO: 33)
FY Exon 2
ACGCACGTCCACGGTGATTTGGGGGCAGCTGCTTCCAGGTTGGCA (SEQ ID NO: 34)
JK Exon 9
CGTGCCGCTCGTGATAGAATAAACCCCAGAGTCCAAAGTAGATGT (SEQ ID NO: 35)
D1 Exon 19
GGCTATGATTCGCAATGCTTGTGCTGTGGGTGGTGAAGTCCACGC (SEQ ID NO: 36)

-continued

GP3A Exon 3
AGAGCGAGTGACGCATACTTGGGCTCCTGTCTTACAC (SEQ ID NO: 37)

GP3A Exon 3
GCCCTGCCTC

The above probes may be referred to herein as SEQ ID NOs 25-37. The DNA bases are represented by their single letter equivalents (A,C,G or T) and SEQ ID NOs: 36 and 37 are joined together by a C3 (phosphoramidite) spacer between the two sequences represented by letter X as follows AGAGCGAGTGACGCATACTTGGGCTCCT-GTCTTACAXGCCCTGCCT (SEQ ID NO. 36×SEQ ID NO. 37).

In this embodiment, the 12 bolded nucleotides in the 5' region of the extension probes are hybridized to a complementary DNA sequence that has been micro-arrayed onto microplates so that specific blood group SNPs are individually identified and reported.

Proof of principle experiments have been performed using 372 consent qualified samples (please refer to Appendix A). Collection of serological data for samples has been constant and the success rates based upon the expected allele frequencies have been performed.

In the preceding example, one preferred embodiment has been described. However, it should be obvious to one skilled in the art that other methodologies and/or technologies for SNP identification could be used, providing that the novel DNA sequences disclosed above are also used.

The teachings and method of the present invention are superior to the teachings of the prior art for a number of reasons, one of which is that the complete method of the present invention, from DNA extraction to result computation analyses can be automated and multiplexed so that many SNPs can be determined simultaneously. This automated multiplex high throughput analysis can meet the demand (hundreds of blood donations can be tested) and the turn-around time (<24 hours) to collate and provide valuable information to the blood collection facility before blood is shipped to the end user. This platform and method has the further advantage over existing technology in that it reduces operator handling error.

In addition, there are significant cost reductions compared with the current technology. The invention addresses the need for an automated, accurate, rapid and cost-effective approach to the identification of multiple blood group SNPs. According to an embodiment, a multiplex SNP assay of the present invention detected 12 SNPs overnight on 372 individual blood samples. In accordance with the teachings of the present invention, the platform, products and methods of the present invention can detect all SNP variations for all blood group antigens, for example, as shown below on 744 samples.

BRIEF DESCRIPTION OF THE DRAWINGS

Further features and advantages of the present invention will become apparent from the following detailed description, taken in combination with the appended drawings, in which.

Figure 1:
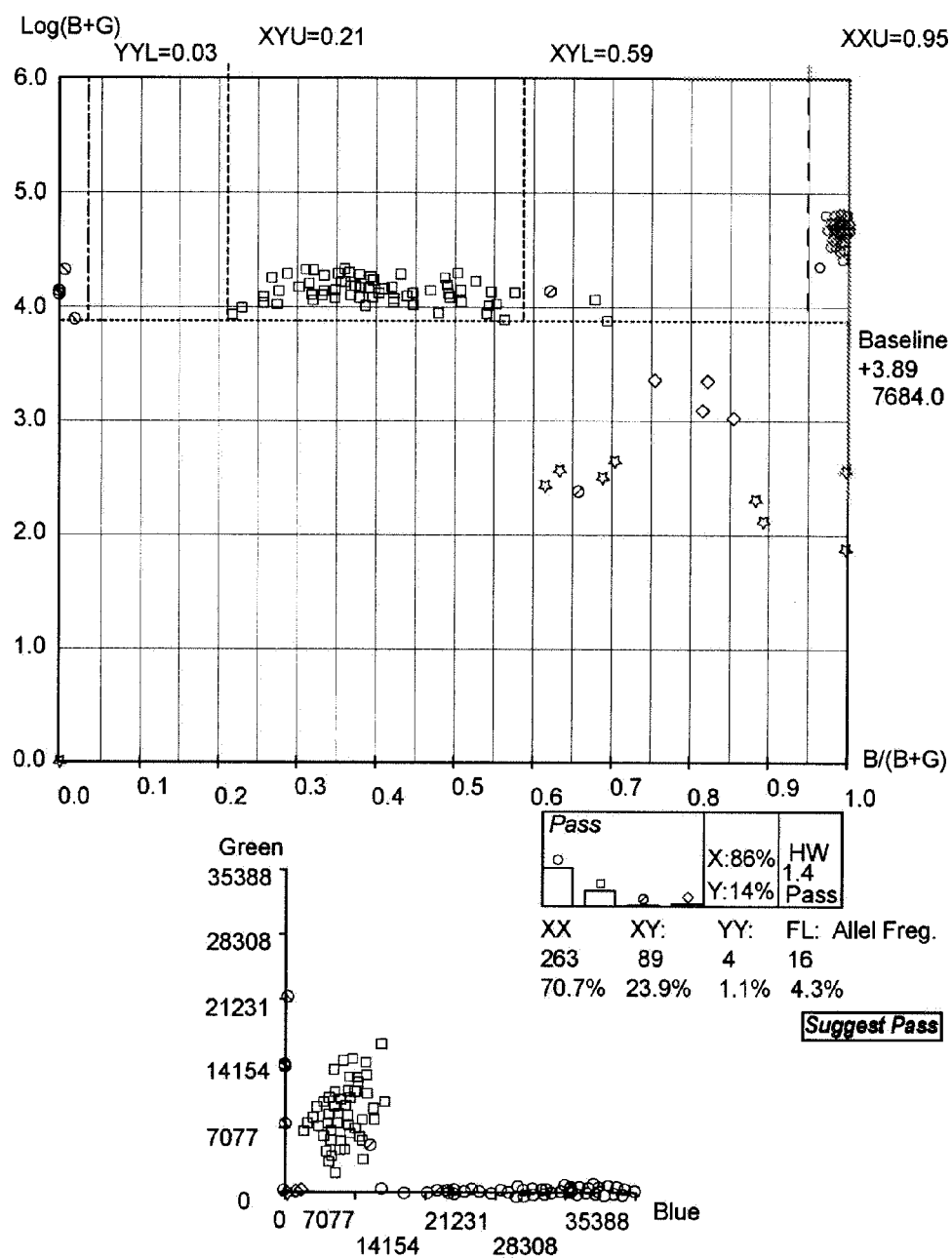
FIG. 1 A computer screen display of a typical UHT SNP scatter plot to sort the fluorescence of a C/T SNP analysis of GP3A Exon 3 for HPA-1a/b genotyping.

Appendix A provides a tabulated summary of the multiplex SNP assay detection of 12 possible SNPs on 372 individual blood samples.

It will be noted that throughout the appended drawings, like features are identified by like reference numerals.

DETAILED DESCRIPTION OF THE PREFERRED EMBODIMENT

RBC and platelet (Plt) alloimmunization requires antigen-matched blood to avoid adverse transfusion reactions. Some blood collection facilities use unregulated Abs to reduce the cost of mass screening, and later confirm the phenotype with government approved reagents. Alternatively, RBC and Plt antigens can be screened by virtue of their associated single nucleotide polymorphisms (SNPs). The present invention provides a multiplex PCR-oligonucleotide extension assay using the GenomeLab SNPStream platform, or any other SNP analysis system, to genotype blood for a plurality of common antigen-associated SNPs, including but not limited to: RhD (2), RhC/c, RhE/e, S/s, K/k, $Kp^{a/b}$, Fya/b, FY0, $Jk^{a/b}$, $Di^{a/b}$, and HPA-1a/b. According to one example of the present invention, a total of 372 samples were analysed for 12 SNPs overnight. Individual SNP pass rates varied from 98-100% for 11 of 12 SNPs. Of the Rh-pos, 98.6% were correctly identified. Six of 66 Rh-neg (9%) were typed as RHD-pos; 5 of 6 were subsequently demonstrated to contain an non-RHDψ gene by SSP-PCR. Eleven of 12 R1R1 and 1 of 1 r"r were correctly identified. HPA-1b was identified in 4, which was confirmed by PCR-RFLP (n=4) and serology (n=1). PCR-RFLP on selected samples (n<20) for K/k, $Fy^{a/b}$, and $Jk^{a/b}$ were 100% concordant. Confirmation of some of the results is provided. The platform has the capacity to genotype thousands of samples per day for all SNP variations. The suite of SNPs can provide collection facilities with real-time genotypic data for all donors at an annual cost (excluding RhD) estimated to equal the current cost of phenotyping 5-10% of the donors.

Methods and Reagents

Methodology Specific to the Invention.

We have designed a novel blood group and HPA SNP and detection system that employ the use of two sets of novel compounds (reagents) that are specifically designed to work in a multiplex format.

In brief, genomic DNA is harvested the salting out procedure using the Qiagen (Qiagen Inc. Valencia, Calif.) Blood DNA Isolation Kit. Our invention can use any good quality DNA harvested by any one of a variety of methods. For the multiplex PCR, the DNA regions containing all 12 SNPs of interest were PCR-amplified in a single reaction well. Tables 1 and 2 outline the novel PCR primers and extension probes, respectively, used in the assay. Note that the concentration of the various reagents may be adjusted to optimize DNA amplification, and is dependent on but is not limited to: the concentration and quality of the genomic DNA, the concentration of the PCR primers or the type of thermal cycler used for the PCR.

Our current genotyping technology identifies SNPs using single base-pair primer extension using the novel products and protocols of the present invention. In brief, the genomic region surrounding the SNP of interest is PCR-amplified as described above, preferably using one or more, or all of the primer pairs of Table 1. Then, the amplified DNA fragments are used as a template for DNA hybridization using one or more or all the corresponding novel probes of Table 2, and single nucleotide extension (synthesis) based on the nucleotide present at each of the specific SNP sites. The PCR primers pairs in Table 1 represent sequences complementary to DNA regions containing SNPs of interest; of which the exact sequences of each primer pair and mixture of primer pairs have been specifically optimized to amplify genomic DNA of interest as a mixture of 12 primer pairs. Although noted above, Table 2 further summarizes 12 novel extension primers specifically used together to detect the nucleotides of blood group and platelet antigen or HPA SNPs, simultaneously. The extension primers represent a group of 12 novel nucleotide sequences, of which each are a combination of: 1) a unique 5' region necessary to direct hybridization to a micro-arrayed tag located in a specific spot in each microplate well, and 2) a 3' region complementary to and adjacent to a SNP of a PCR-amplified DNA region containing the SNP of interest.

TABLE 1

The PCR primers used in the 12-pair multiplex PCR format for multiple SNP detection.

| Antigen | Primer SNPName | Sequence 5'-3' | Product Target | Size (bp) |
|---|---|---|---|---|
| RhD/RhCE | C/TRHDe4S | AGACAAACTGGGTATCGTTGC | RHD | 111 |
|  | RHDe4A | ATCTACGTGTTCGCAGCCT | Exon 4 |  |
| RhD/RhCE | A/GRHDe9S | CCAAACCTTTTAACATTAAATTATGC | RHD | 98 |
|  | RHDe9A | TTGGTCATCAAAATATTTAGCCTC | Exon 9 |  |
| RhC/Rhc | T/CRHCEe2S | TGTGCAGTGGGCAATCCT | RHCE | 90 |
|  | RHCEe2A | CCACCATCCCAATACCTG | Exon 2 |  |
| RhE/Rhe | C/GRHCEe5S | AACCACCCTCTCTGGCCC | RHCE | 107 |
|  | RHCEe5A | ATAGTAGGTGTTGAACATGGCAT | Exon 5 |  |
| GYPBS/GYPBs | T/CGYPBe4S | ACATGTCTTTCTTATTTGGACTTAC | GPYB | 103 |
|  | T/CGYPBe4A | TTTGTCAAATATTAACATACCTGGTAC | Exon 4 |  |
| K/k | T/CKELe6S | TCTCTCTCCTTTAAAGCTTGGA | KEL | 142 |
|  | KELe6A | AGAGGCAGGATGAGGTCC | Exon 6 |  |
| KP$^a$/KP$^b$ | T/CKELe8S | AGCAAGGTGCAAGAACACT | KEL |  |
|  | KELe8A | AGAGCTTGCCCTGTGCCC | Exon 8 100 |  |
| Fy/Fy0 | T/CFYproS | TGTCCCTGCCCAGAACCT | Duffy | 90 |
|  | FYproA | AGACAGAAGGGCTGGGAC | Promoter |  |
| FY$^a$/FY$^b$ | G/AFYe2S | AGTGCAGAGTCATCCAGCA | Duffy | 122 |
|  | FYe2A | TTCGAAGATGTATGGAATTCTTC | Exon 2 |  |
| Jk$^a$/Jk$^b$ | G/AJKe9S | CATGAACATTCCTCCCATTG | Kidd | 130 |
|  | JKe9A | TTTAGTCCTGAGTTCTGACCCC | Exon 9 |  |
| Di$^a$/Di$^b$ | T/CDIe19S | ATCCAGATCATCTGCCTGG | Diego | 90 |
|  | Die19A | CGGCACAGTGAGGATGAG | Exon 19 |  |
| HPA-1a/b | T/CGP3Ae3S | ATTCTGGGGCACAGTTATCC | GP3A | 114 |
|  | GP3Ae3A | ATAGTTCTGATTGCTGGACTTCTC | Exon 3 |  |

The above primers correspond to SEQ ID NOs 1-24. respectively, as outlined herein above.

TABLE 1A

Additional Blood Group and Platelet Antigen SNPs for Clinically Relevant Antigens.

| Antigen | SNP | Product Target | Size (bp) |
|---|---|---|---|
| A/O GalNAc/Del | G/T | ABO Exon 6 | |
| A/B (GalNAc/Gal) | C/G | ABO Exon 7 | |
| A/B (GalNAc/Gal) | G/A | ABO Exon 7 | |
| A/B (GalNAc/Gal) | C/A | ABO Exon 7 | |
| A/B (GalNAc/Gal) | G/C | ABO Exon 7 | |
| M/N | G/A | MNS Exon 2 | |
| M/N | T/G | MNS Exon 2 | |
| MNS/Mi I | C/T | MNS Exon 3 | |
| RHD/Weak D Type 1 | T/G | RHD Exon 6 | |
| RHD/Weak D Type 2 | G/C | RHD Exon 9 | |
| RHD/Weak D Type 3 | C/G | RHD Exon 1 | |
| RHD/D nt602 Variants | C/G | RHD Exon 4 | |
| RHD/'DAR' Variant | T/C | RHD Exon 7 | |
| RHD/Weak D Type 5 | C/A | RHD Exon 3 | |
| RHD/$D_{el}$ | G/A | RHD IVS3 + 1 | |
| RHD/$D_{el}$ | G/T | RHD Exon 6 | |
| RHD/$D_{el}$ | G/A | RHD Exon 9 | |
| RHD/RHDψ nt506 | A/T | RHD Exon 4 | |
| RHCE/RhC | T/C | RHCE IVS2 + 1722 | |
| RHCE/RhC | C/T | RHCE IVS2_1751 | |
| RHCE/ VS variant | C/G | RHCE Exon 5 | |
| $Lu^a/Lu^b$ | A/G | LU Exon 3 | |
| $Au^a/Au^b$ | A/G | LU Exon 12 | |
| $Js^a/Js^b$ | C/T | KEL Exon 17 | |
| Js/Js$_{null}$ | G/T | JK IVS7 + 1 | |
| FY/Fy$^x$ | C/T | FY Exon 2 | |
| FY/Fy$^x$ | G/A | FY Exon 2 | |
| $Wr^a/Wr^b$ | A/G | DI Exon 16 | |
| $Yt^a/Yt^b$ | C/A | YT Exon 2 | |
| Sc1/Sc2 | G/A | SC Exon 3 | |
| $Do^a/Do^b$ (nt 378) | C/T | DO Exon 2 | |
| $Do^a/Do^b$ (nt 624) | T/C | DO Exon 2 | |
| $Do^a/Do^b$ (nt 793) | A/G | DO Exon 2 | |
| $Co^a/Co^b$ | C/T | CO Exon 1 | |
| $In^a/In^b$ | C/G | IN Exon 2 | |
| Ok(a+)/Ok(a−) | G/A | OK Exon 4 | |
| GIL/GIL$_{null}$ | G/A | GIL IVS5 | |
| HPA-2a/b | C/T | GP1BA Exon 2 | |
| HPA-3a/b | T/G | GP2B Exon 26 | |
| HPA-4a/b | G/A | GP3A Exon 4 | |
| HPA-5a/b | G/A | GP1A Exon 13 | |
| Gov$^a$/Gov$^b$ | A/C | CD109 Exon 19 | |

Each antigen listed on the left represents a blood group or HPA genotype and the single nucleotide polymorphism (SNP). Some genotypes are evaluated using more than one SNP because they differ by more than one nucleotide. Each PCR primer pair consists of a sense (Primer Name ending in S) and antisense (Primer Name ending in A) oligonucleotide (Sequence 5'-3') designed to amplify the DNA region containing the SNP for the antigen of interest. The target region (Product Target) and the amplified fragment (Size (bp)) are shown on the right. Note that 12 SNPs are evaluated for 19 different blood group and platelet antigens because some antigens have more than one SNP. In some cases an A or G SNP is included since the complementary DNA strand can be evaluated as it will contain the T or C SNP of interest.

TABLE 2

Extension probes used to detect the nucleotides of blood group and HPA SNPs.

| Name | Sequence 5'-3' |
|---|---|
| RHD Exon 4 | GTGATTCTGTACGTGTCGCCGTCTGATCTTTATCCTCCGTTC CCT |
| RHD Exon 9 | GCGGTAGGTTCCCGACATATTTTAAACAGGTTTGCTCCTAAA TCT |
| RHCE Exon 2 | GGATGGCGTTCCGTCCTATTGGACGGCTTCCTGAGCCAGTTC CCT |
| RHCE Exon 5 | CGACTGTAGGTGCGTAACTCGATGTTCTGGCCAAGTGTCAAC TCT |
| GYPB Exon 4 | AGGGTCTCTACGCTGACGATTTGAAATTTTGCTTTATAGGAG AAA |
| KEL Exon 6 | AGCGATCTGCGAGACCGTATTGGACTTCCTTAAACTTTAACC GAA |
| KEL Exon 8 | AGATAGAGTCGATGCCAGCTTTCCTTGTCAATCTCCATCACT TCA |
| FY Promoter | GACCTGGGTGTCGATACCTAGGCCCTCATTAGTCCTTGGCTC TTA |
| FY Exon 2 | ACGCACGTCCACGGTGATTTGGGGGCAGCTGCTTCCAGGTTG GCA |
| JK Exon 9 | CGTGCCGCTCGTGATAGAATAAACCCCAGAGTCCAAAGTAGA TGT |
| Di Exon 19 | GGCTATGATTCGCAATGCTTGTGCTGTGGGTGGTGAAGTCCA CGC |

TABLE 2-continued

Extension probes used to detect the
nucleotides of blood group and HPA SNPs.

| Name | Sequence 5'-3' |
|---|---|
| GP3A Exon 3 | AGAGCGAGTGACGCATACTTGGGCTCCTGTCTTACAXGCCCT *GCCTC* |

The above probes correspond to SEQ ID NOs 25-36, respectively, as identified herein above.
The DNA bases are represented by their single letter equivalents (A, C, G or T) and the letter X represents a C3 (phosphoramidite) spacer between the two adjacent DNA bases.

The above probes correspond to SEQ ID NOs 25-37, respectively, as identified herein above. The DNA bases are represented by their single letter equivalents (A,C,G or T) and the letter X in GP3A, Exon 3, between the SEQ ID NO. 36 and SEQ ID NO: 37 represents a C3 (phosphoramidite) spacer between the two adjacent DNA bases.

The present invention also provides novel hybrid probes, wherein the preferred probes are listed in Table 2, but limited to said listing. Each extension probe is designed in two parts: (1) the 5' portion: the 5' nucleotides indicated in boldface of the extension primer are complementary to unique and specific DNA sequences which are micro-arrayed onto the bottom of microplates in a specified location of each microplate well. Thus, the 5' portion of the extension probes in table 2 represent, but are not limited to, 12 unique complementary sequences used together to identify the individual SNPs through hybridization to the micro-arrayed tags in the microplate wells. The 12 unique 5' portions can be interchanged with each of the 3' regions specified below, which contain DNA sequences complementary to and adjacent to the SNPs of interest, or they can be interchanged with other additional unique 5' portions as specified by the micro-arrayed tags in the microplate wells provided they are used to identify blood group or HPA SNPs; and (2) the 3' portion: the 3' nucleotides are complementary to and precisely adjacent to the SNP site of the PCR-amplified DNA, which enables the detection of either or both nucleotides of the SNP. Thus, the extension probe is a unique sequence that can hybridized to a specific location and to the PCR-amplified DNA and be extended by a single fluorescent-labeled dideoxy-nucleotide using PCR thermal cylers. The extension probe products are hybridized to the complementary micro-arrayed DNA sequence on the microplate and the incorporation of Bodipy- and Tamra-labeled dideoxy-nucleotides are detected by laser-microplate fluorescence for each individual blood group SNP. The presence of the nucleotides for a given SNP is displayed by automated imaging and analysis software. In one variation of the detection reaction, a dideoxyguanidine tri-nucleotide labeled with the Bodipy-fluorochrome is added in the extension reaction. If a deoxycytidine is present in the PCR-amplifed DNA fragment, then the nucleotide will be incorporated into the nascent DNA fragment. In another variation of the reaction, a dideoxyadenine nucleotide labeled with the Tamra-fluorochrome is added to the extension assay. If the PCR-amplified fragment contains a deoxythimidine, then an extension will occur. In each case, the flurochrome is detected after the extension reaction has been completed. Again, these reactions proceed in the same tube along with the other extension reactions. The laser-detection apparatus can identify and evaluate each specified extension due to the location of each micro-arrayed DNA sequence.

Each extension primer has a region complementary to a tag that is been bound to the surface of a microplate well (Bold nucleotides) and a region (Italicized nucleotides) that is complementary to the region and immediately adjacent to the SNP site.

It should be noted that the teachings, products and methods of the present invention are not limited to the above-specified primer pairs and probes, but additionally comprise all primer pairs and probes specific to the blood group and HPA SNPs, wherein said primer pairs and probes are optimized for use in a multiplex PCR reaction for the simultaneous identification of more than one, or all, blood group or HPA genotypes and their corresponding phenotypes.

EXAMPLES

Although the following examples may provide preferred methods, products, platforms or protocols of the present invention, it will be understood by one skilled in the art that the presently provided examples are not limited to the specified parameters of each example, and may be varied provided that the resulting outcome of the methods or protocols are in accordance with the teachings of the present invention, and the products are functionally equivalent or relating to the teachings of the present invention.

Example 1

A preferred protocol for the multiplex blood group and HPA SNP Genotyping is provided. Although the present example analyzes 12 SNP extension primers, the present invention is not limited to the analysis of a maximum of 12 SNPs, but may include a plurality of SNPs relating to more than one or all of the blood group or HPA SNPs.

Additional blood group and platlet antigen SNPs for clinically relevant antigens embodied by the present invention appear in Table 1A. Primer pairs and probes, such as those exemplified in Tables 1 and 2, corresponding to these SNPs of clinical relevance, can be prepared according to the teachings of the present invention. Target primers may be initially identified from existing databases (e.g. autoprimer.com) based on information corresponding to the SNP of interest and the corresponding flanking regions, and subsequently optimized as herein disclosed for use in accordance with the present invention.

I (a). PCR Primer Pooling

| Step | Action |
|---|---|
| 1 | Dilute each of 12 PCRS and PCRA primer (forward and reverse primers) pairs to final concentration of 240 uM (only required upon arrival of new primers) |
| 2 | Generate working primer pool by combining 5 ul of each of the 24 individual PCR primers |

I (b). SNP Extension Primer Pooling

| Step | Action |
|---|---|
| 1 | Dilute each of 12 SNP extension primers to final concentration of 120 uM (only required upon arrival of new primers) |
| 2 | Generate working SNP extension primer pool by combining 10 ul of each of the 12 individual SNP extension primers |

| | II. Multiplex PCR from purified DNA templates | |
|---|---|---|
| Step | Action | |

1. Prepare 10 ul multiplex PCR master mix for use with 96 well plates containing PCR primers (synthesized by Integrated DNA Technologies, Coralville, IA, USA), dNTPs (MBI Fermentas, Hanover, MD, USA), $MgCl_2$, 10X PCR Buffer, and Amplitaq Gold (Applied Biosystems, Branchburg, NJ, USA):

| Component | Initial Concentration | Final Concentration | Volume (ul/well) |
   |---|---|---|---|
   | PCR primer pool | 10 uM each | 50 nM each | 0.05 |
   | dNTPs | 2.5 mM each | 75 uM each | 0.33 |
   | $MgCl_2$ | 25 mM | 5 mM | 2.00 |
   | 10x PCR Buffer | 10x | 1x | 1.00 |
   | AmpliTaq Gold | 5 U/ul | 0.075 U/ul | 0.15 |
   | $dH_2O$ | | | 4.47 |

2. For each DNA Sample, transfer 2 ul of 4 ng/ul stock DNA to each well of 96 well plates. Use Biomek FX (Beckman Coulter Inc., Fullerton, CA, USA) Script '2ul96well Transfer' automated program
3. Place Multiplex PCR Master Mix in Biomek FX station 1. Place 96 well plates of DNA in Biomek FX station 5-8.
4. Transfer 8 ul Multiplex PCR master mix to DNA samples using Biomek FX Script: '8ul PCR Transfer'
5. After addition of master mix seal tightly with MJ Microseal A film (MJ Research, Inc., Waltham, MA, USA)
6. Spin down in centrifuge for 30 sec at 1500 rpm
7. Place in MJ Tetrad Thermal cyclers (MJ Research, Inc., Waltham, MA, USA)and run 'UHT-MPX' CBS multiplex PCR program:

Thermal cycle conditions 'UHT-MPX':

| | | |
   |---|---|---|
   | Denature | 94° C. | 1:00 (min) |
   | 35 cycles of: | 94° C. | 0:30 (min) |
   | | 55° C. | 0:33 (min) |
   | | 72° C. | 1:00 (min) |
   | Hold Temperature | 4° C. | ∞ |

| | III. Post PCR Cleanup | |
|---|---|---|
| Step | Action | |

1. Prepare ExonucleaseI (ExoI; USB Corporation, Cleveland, OH, USA) and Shrimp Alkaline Phosphatase (SAP; USB Corporation, Cleveland, OH, USA) master mix:

| Component | Final concentration | Volume per well (ul) |
   |---|---|---|
   | ExoI | 2 U | 0.4 |
   | SAP | 1 U | 2.0 |
   | 10x SAP buffer | 1x | 0.6 |
   | $dH_2O$ | | 3.0 |

2. Add Exo/SAP master mix to grooved reservoir and place on Multimek (Beckman Coulter Inc., Fullerton, CA, USA) Station 3
3. Add UHT (ultra high-throughput) salt solution (provided) to grooved reservoir and place on Multimek Station 4
4. Transfer 8 ul Exo/SAP master mix to amplified PCR products using Multimek Script: EXO96-2.SCI (two 96 well plates, at Multimek stations 1 and 2
5. After Multimek addition of Exo/SAP seal tightly with MJ Microseal A film
6. Spin down in centrifuge for 30 sec at 1500 rpm
7. Place in MJ Tetrad Thermal cyclers and run 'UHTCLEAN' program:

Thermal cycle conditions 'UHTCLEAN':

| Temp | Time (min) |
   |---|---|
   | 37° C. | 30:00 |
   | 100° C. | 10:00 |
   | 4° C. | ∞ |

IV. SNP-IT Assay using the GENOMELAB SNPSTREAM ™ (Beckman Coulter Inc. Fullerton, CA, USA)

| Step | Action |
|---|---|
| 1 | Prepare SNP-IT extension mix containing extension primers (synthesized by Integrated DNA Technologies, Coralville, IA, USA), C/T ddNTPs, Extension mix diluent, and DNA polymerase (Beckman Coulter Inc., Fullerton, CA, USA) |

| Component | Volume per well (ul) |
|---|---|
| SNP Extension primer pool | 3.22 |
| C/T ddNTP Extension mix | 21.43 |
| Extension mix diluent | 402.98 |
| DNA polymerase | 2.24 |
| dH2O | 318.22 |

| Step | Action |
|---|---|
| 2 | Add SNP-IT mix to grooved reservoir and place on Multimek Station 3 |
| 3 | Add UHT salt solution (provided) to grooved reservoir and place on Multimek Station 4 |
| 4 | Transfer 7 ul SNP-IT extension mix to UHT-CLEAN PCR products using Multimek Script: 7UL96-2.SCI (two 96 well plates, at Multimek stations 1 and 2 |
| 5 | After Multimek addition of SNP-IT extension mix seal tightly with MJ Microseal A film |
| 6 | Spin down in centrifuge for 30 sec at 1500 rpm |
| 7 | Place in MJ Tetrad Thermal cyclers and run 'UHT-SNPIT' program: |

Thermal cycle conditions 'UHTSNPIT':

| | Temp | Time (min) |
|---|---|---|
| Denature | 96° C. | 3:00 |
| 45 cycles of: | 94° C. | 0:20 |
| | 40° C. | 0:11 |
| Hold Temperature | 4° C. | ∞ |

V. Post-extension Transfer and Hybridization

| Step | Action |
|---|---|
| 1 | Preheat incubator to 42° C. |
| 2 | Make sure there is adequate 20x dilution of SNPWare UHT Wash Buffer in washer Carboy B. If required dilute 20x stock solution with water and refill Carboy B |
| 3 | Run SAMI/EL 405 Script 'Prime B' |
| 4 | Place all Tag Array plates in Row 1 of the Carousel, starting with Hotel 1, with subsequent plates in Hotel 2, 3, etc., preferably with their barcodes facing inwards. |
| 5 | Place all PCR plates directly below their corresponding Tag Array Plates. PCR plates corresponding to Quadrants 1-4 should be placed in Rows 2-5 of the proper Hotel, respectively. For all PCR plates, the "ABC . . . " lettered edge of the plates should face inwards on the Carousel. |
| 6 | Place grooved reservoir with solubilized UHT Salt Solution in Multimek Station 4 |
| 7 | Place grooved reservoir with Hybridization solution master mix in Multimek Station 3
Hybridization Solution master mix: |

| Component | Volume per Tag Array plate (ul) |
|---|---|
| 2x Hybridiaztion Soluton | 3500.00 |
| Hybridization Additive | 203.7 |

| Step | Action |
|---|---|
| 8 | Run SAMI Script 'Post-extension Transfer_Hybridization 1x384.smt': This automated program prepares the tag array plate by washing it 3x with SNPWare UHT wash buffer; adds 8.0 ul of Hybridization solution master mix to each SNP extension reaction and subsequently transfers 8.0 ul of this mixture to the prepared tag array plate. |
| 9 | Place Tag Array plates in humidified 42° C. incubator for 2 hours |

| VI. Post-Hybridization Wash | |
|---|---|
| Step | Action |
| 1 | Make sure there is adequate 64x dilution of SNPWare UHT Stringent Wash Solution in washer Carboy C. If required dilute 64x stock solution with water and refill Carboy C |
| 2 | Run SAMI/EL 405 Script 'Prime C' |
| 3 | Run SAMI/EL 405 Script 'Post-hyb 3x Wash' |
| 4 | Completely dry Tag Array plates using vacuum/pipette tip |
| 5 | Run SAMI/EL405 script 'Prime A' several times to clean plate washer pins |

| VII. UHT (Ultra high through-put) Tag Array Plate Reading | |
|---|---|
| Step | Action |
| 1 | Turn on lasers, turning both keys 90 degrees clockwise, and allow at least 30 minutes to warm up |
| 2 | Turn on SNPScope Reader and Twister. |
| 3 | Activate lasers: Flip two switches on laser box from 'Standby' to 'Operate'/'Laser' |
| 4 | Open UHT Run Manager Software and 'Initialize' SNPScope system |
| 5 | Stack Tag Array plates in Twister carousel 1, with 'Assay Test Plate' on top. Make sure all barcodes are facing outwards, and plates are pushed towards the reader |
| 6 | Select 'SNPTEST_W_BC_run' from UHT RUN Manager Software, enter the number of plates to be read (including the test plate). |
| 7 | Select 'RUN' |

The SNPScope plate reader will excite and capture images of Bodipy-fluorescein and Tamra-labeled ddNTPs separately. All genotype calls are subsequently automatically generated using the SNPStream Software Suite of MegaImage, UHT-GetGenos and QCReview.

It should be noted that the specific steps associated with the protocol exemplified in Example 1 are not intended to limit the teachings and methods of the present invention to the specific above protocol. Example 1 is provided to specify a preferred method in accordance with the present invention wherein a plurality of blood group and HPA SNPs are simultaneously analysed in a ultra high throughput multiplex automated system for the determination of the specific genotypes and accordingly the phenotypes associated therewith. Accordingly, it should be understood by one skilled in the art that the steps of Example 1 may be varied provided that such variations yield the preferred results of the present invention.

Results

1. GP3A Exon 3 SNP Scatter Plots

The robotic UHT platform produces laser-fluorescence values for each sample which are represented in 'scatter plots' for the operator to review. A sample scatter plot is shown in FIG. 1 for the SNP analysis GP3A Exon 3, which represents the HPA-1a and HPA-1b antigens. As can been seen in FIG. 1 and FIG. 4, results are graphed using logarithmic and XY scatter plots (upper right). Green O, orange □ or blue O sample designations represent CC, TC and TT SNP genotype calls, respectively, with corresponding graphical summaries appearing in the respective legends of each figure. No fluorescence represents an assay failure (FL) for that sample.

Scatter plots (as shown in FIG. 1 and FIG. 4) are generated preferably using SNPStream software suite and viewed through QCReview. It should be additionally noted that the present analysis is not limited to SNPstream or QCReview, and may be carried out using any SNP analysis software. Individual TT, TC and CC genotype calls are represented as dark blue, orange and green open circles, respectively. Sample failures and water controls are represented by yellow and light blue filled circles respectively. Logarithmic (left) and XY scatter (upper right) plots are generated using the relative fluorescence of the Bodipy-fluorescein and Tamra labels obtained during SNPScope plate imaging and analysis.

2. SNP Data Manipulation and Analysis

The SNP results of a scatter plot are electronically exported to a spreadsheet and examined for total sample failure and individual SNP failure rates. SNP results for 372 DNA samples are summarized in Table 3 (provided in Appendix A). Accordingly, Table 3 provides the Pass and Failure Rates for 12 blood group and HPA SNP analyses. 372 DNA samples were analyzed for several antigens, including the blood group RhD (RHD Exon 4 and RHD Exon 9) and platelet HPA-1a/b (GP3A Exon 3) genotypes. Sample success or pass rates are indicated on the right and individual SNP success or pass rates are shown at the bottom. Three hundred and fifty seven of 372 samples (96%) had results for at least one SNP. Individual SNP results (i.e. minus the sample failures) ranged from 80-100%; only two SNPs had success rates <98%. Individual SNP failures do not affect the results of a sample for other SNPs that do not fail.

3. SNP Allele Result Compared to the Serological Result

RhD status was compared between the serological result and the SNP analysis for RHD Exon 4 and RHD Exon 9. Table 4 summarizes the comparison. 287 of 291 (98.6%) RhD positive units and 55 of 66 (83.3%) RhD negative units were identified correctly using the UHT SNP platform. It is important to note that the 6 incorrect calls suggesting the presence of the RHD gene in a serologically RhD-negative sample may be due to one of the non-functional RHD genes present in the random population (Singleton B. K. et al., Blood 2000; 95:12; Okuda H., et al., J Clin Invest 1997; 100:373; Wagner F. F. et al., BMC Genet 2001; 2:10).

TABLE 4

A comparison of the SNP genotype result and the serological result obtained with government-regulated antisera.

| Assay | RHD Exon 4 | RHD Exon 9 | No | Percent |
|---|---|---|---|---|
| D-positive: | pos | Pos | 287 | 98.6% |
| N = 291 | neg | Neg | 4 | 1.4% |
| Total | | | 291 | |

| Assay | RHD4 | RHD9 | No | Percent |
|---|---|---|---|---|
| D-negative: | neg | Neg | 55 | 83.3% |
| N = 66 | neg | FL | 5 | 7.6% |
| | pos | Pos | 6 | 9.1% |
| Total | | | 66 | |

NOTE:
CBS laboratory regulations do not allow copies of serological results of blood donors to be made from their laboratory information system. Therefore, the results of the CBS serological phenotypes were reviewed by research personnel and the results tabulated and compared to the SNP data.

4. SNP Genotype Frequency Analysis

The SNP results then were compared with published phenotype frequencies for Caucasians and Blacks and are summarized in Table 5 below. The data clearly shows that the allele frequencies are consistent with the accepted published frequencies for Caucasians and Blacks. The data show that the SNP genotype frequencies match the published population phenotype frequencies.

TABLE 5

Table 5. A summary of the UHT SNP analysis of genotype frequencies for several SNPs analyzed and compared to published phenotype frequencies for Caucasians and Blacks. The ethnicity of the samples analyzed is not known.

UHT Genotyping Analysis
KEL Exon6

| Phenotype | Caucasians | Blacks | Observed | (%) |
|---|---|---|---|---|
| K−k+ | 91% | 98% | 326 | 91.3 |
| K+k− | 0.2% | rare | 0 | 0 |
| K+k+ | 8.8% | 2% | 28 | 7.8 |
| Fails | | | 3 | 0.8 |
| No of FL | 18 | | | |
| No. of Pass | 354 | | | |
| Call Rate | 95.2% | | | |

FL = assay failure
An independent assay as described in Molecular Protocols in Transfusion Medicine was performed using the UHT SNP Stream System.

TABLE 5-continued

Seven samples were tested (Four KEL 2/KEL 2, Three KEL1/KEL 2).
All samples showed a 100% correspondence with the UHT genotype results.

KEL Exon8

| Phenotype | Caucasians | Blacks | Observed | (%) |
|---|---|---|---|---|
| Kp(a+b−) | Rare | 0% | 0 | 0 |
| Kp(a−b+) | 97.7% | 100% | 354 | 99.2 |
| Kp(a+b+) | 2.3% | rare | 1 | 0.3 |
| Fails | | | 2 | 0.6 |
| No of FL | 17 | | | |
| No. of Pass | 355 | | | |
| Call Rate | 95.4% | | | |

DI Exon18

| Phenotype | Caucasians | Blacks | Observed | (%) |
|---|---|---|---|---|
| Di(a+b−) | <0.01% | <0.01% | 0 | 0 |
| Di(a−b+) | >99.9% | >99.9% | 353 | 98.9 |
| Di(a+b+) | <0.1% | <0.1% | 2 | 0.6 |
| Fails | | | 2 | 0.6 |
| No of FL | 17 | | | |
| No. of Pass | 355 | | | |
| Call Rate | 95.4% | | | |

FY PRM

| Phenotype | Observed | (%) |
|---|---|---|
| wt/wt | 348 | 97.5 |
| wt/mut | 7 | 20 |
| mut/mut | 2 | 0.5 |
| Fails | 0 | 0 |
| No of FL | 15 | |
| No. of Pass | 357 | |
| Call Rate | 96.0% | |

An independent assay as described in Molecular Protocols in Transfusion Medicine was performed using the UHT SNP Stream System.
Thirteen samples were tested (six wt/wt, five wt/mut and two mut/mut for the GATA site).
All samples showed a 100% correspondence with the UHT genotype results.

FY Exon 2

| Phenotype | Caucasians | Blacks | Observed | (%) |
|---|---|---|---|---|
| Fy(a+b−) | 17% | 9% | 89 | 24.9 |
| Fy(a−b+) | 34% | 22% | 112 | 31.4 |
| Fy(a+b+) | 49% | 1% | 155 | 43.4 |
| Fails | | | 1 | 0.3 |
| No of FL | 16 | | | |
| No. of Pass | 356 | | | |
| Call Rate | 95.7% | | | |

An independent assay as described in Molecular Protocols in Transfusion Medicine was performed using the UHT SNP Stream System
Eleven samples were tested (eight FY2/FY2, three FY1/FY2 and one FY1/FY1).
All samples showed a 100% correspondence with the UHT genotype results.

GP3A Exon 3

| Phenotype | Caucasians | Blacks | Observed | (%) |
|---|---|---|---|---|
| HPA-1a/1a | 80% | 84% | 263 | 73.7 |
| HPA-1a/1b | 18% | 64% | 89 | 24.9 |
| HPA-1b/1b | 2% | 0% | 4 | 1.1 |
| Fails | | | 1 | 0.3 |
| No of FL | 16 | | | |

TABLE 5-continued

| No. of Pass | 356 |
| Call Rate | 95.7% |

An independent assay as described in Molecular Protocols in Transfusion Medicine was performed using the UHT SNP Stream System.
Eighteen samples were tested (Seven HPA-1a, Seven HPA-1a/1b and Four HPA-1b).
All samples showed a 100% correspondence with the UHT genotype results.

JK9

| Phenotype | Caucasians | Blacks | Observed | (%) |
| --- | --- | --- | --- | --- |
| Jk(a+b−) | 26.3% | 51.1% | 90 | 25.2 |
| Jk(a−b+) | 23.4% | 8.1% | 87 | 24.4 |
| Jk(a+b+) | 50.3% | 40.8% | 178 | 49.4 |
| Fails | | | 2 | 0.5 |
| No of FL | 17 | | | |
| No. of Pass | 355 | | | |
| Call Rate | 95.4% | | | |

An independent assay as described in Molecular Protocols in Transfusion Medicine was performed using the UHT SNP Stream System.
Nineteen samples were tested (Seven JK1, Seven JK1/JK2 and Five JK2).
All samples showed a 100% correspondence with the UHT genotype results.

5. HPA-1a/HPA-1b PCR-RFLP Analysis

Figures 2A, 2B:
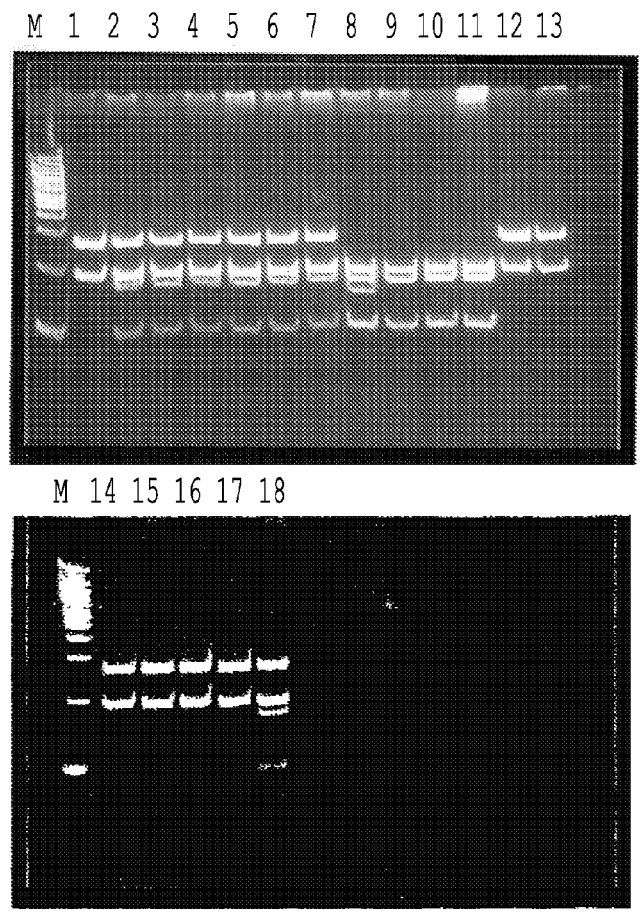
FIG. 2 Representative samples of GP3A Exon 3 HPA-1a/b) genotyping by manual PCR-RFLP analysis using MspI restriction enzyme analysis (A) and the tabulated comparative results with the UHT SNP analysis (B).

The GP3A Exon 3 SNP detection method for HPA-1a/b genotyping (Appendix A) was compared to a subset of samples (n=18) using conventional PCR-RFLP analysis performed independently (FIG. 2). The results of the two assays were 100% concordant. In addition, a 217G nucleotide mutation 21 basepairs downstream of the GP3A SNP was present in sample 8. This mutation does not affect HPA-1b expression but is detected in the PCR-RFLP and is prone to interpretation error in the conventional PCR-RFLP assay. However, the sample was correctly genotyped as HPA-1b in our SNP assay. Accordingly, the present invention eliminates or minimizes error in HPA-1 results obtained since no confusing or confounding information results from the gel readings of the present invention. That is to say, the conventional RFLP detected the presence of an additional DNA fragment at ~180 bp which represents a heterozygous HPA-1b/1b$^{G217}$ allele and was correctly genotyped as HPA-1b/b by the present invention.

Example 2

However, it should be obvious to one skilled in the art that other methodologies and/or technologies for SNP identification could be used, providing that the novel DNA sequences disclosed above are also used. Other embodiments could include the following but without limitation to micro-arrays on glass slides or silica chips, the use of mass spectrometry, or oligo-ligation and extension techniques to detect the SNPs of interest.

A preferred method of the present invention relates to a method for the detection of blood group and HPA genotypes. The present invention also provides novel DNA sequences that are used as primers in a multiplex PCR format according to the present invention to amplify the genomic regions of interest. The present invention also provides novel combinations of DNA sequences that are used in said multiplex PCR format, and for novel DNA sequences that are used to detect blood group and platelet SNPs.

A preferred application of the present invention is in the blood collection and blood banking industry without limitation to red blood cell, platelet, and bone marrow donations. Canada has over 850,000 blood donations yearly, many from repeat donors. Eventually, after all repeat donors are tested (each donor is tested once), the analyses will be performed only on the blood of new donors. With over 29 blood group and 6 HPA systems encompassing over 250 antigens, the platform will find wide application in this industry.

The present invention additionally encompasses various embodiments relating to the detection of various SNPs for the determination of the various genotypes in a sample and for the determination of the corresponding phenotype. In a preferred embodiment, the present invention utilizes a platform to analyzes a cytidine-to-thymidine (C→T) single nucleotide polymorphism. The invention may also employ the multiplex detection of, but not limited to, C→A, A→T, and G→C SNPs, or any other nucleotide SNP related to blood group or platelet antigens.

The present invention may additionally include methods and products for the detection of clinically relevant blood group antigens whereby an antigen of interest is characterized by a genotypic identifier that exceeds a single nucleotide polymorphism. Specifically, the present invention may extend to include clinically relevant insertions or deletions or other nucleotide changes that characterize a blood group antigen of interest, such a multiple base pair insertion in an allele of interest. For example, a genotypic identifier corresponding to a blood group antigen of interest may be pre-characterized, suitable primers and probes for detection thereof may be prepared and a blood sample screened according to the teachings of the present invention.

The present invention provides DNA sequences corresponding to the PCR primer pairs optimized for multiplex use to identify blood group and platelet antigens simultaneously. Accordingly, the present invention provides the novel primer pair sequences listed in Table 1.

The present invention additionally provides novel DNA sequences used to identify the single nucleotide polymorphisms (SNPs) that represent underlying DNA blood group and platelet antigens. Accordingly, the present invention provides the novel extension probes listed in Table 2.

The present invention provides a method of a combined analysis of blood group and HPA SNP analyses.

The present invention advantageously utilizes PCR, the variant and unique SNPs for the variant alleles that infer blood group phenotypes, and single base extension and detection chemistry as a foundation for the novel products and methods of the present invention. Accordingly, the present invention provides a high throughput, multiplexed, DNA-based method of blood group genotyping that replaces the current manual, semi-automated and automated serological screening process used to determine blood group phenotypes.

Accordingly, the present invention provides a method for the identification of rare blood group genotypes due to the suite of SNPs as described above, and in some instances replaces the current state of the art in which most rare blood group genotypes are identified serendipitously (propositus and their relatives) and enabling significant advances over current serological technologies. For example, by analyzing the SNP for the RhC allele in Rh negative blood, we can identify RhC homozygotes and thereby, the rare RhD-negative and Rhc-negative blood.

The present invention additionally provides a method of use in tissue compatibility matching for the purposes, without limitation, of organ transplantation, bone marrow transplantation and blood transfusion related to blood group and platelet antigens.

The present invention additionally provides novel components and constituents that are beneficial for the analyses relating to the present invention. More specifically, the group of currently developed SNPs representing a 'suite', or the presently known set of SNPs that relate to clinically important blood group and HPA genotypes for red blood cell and platelet antigens, respectively are provided. The present invention is not limited to the presently listed SNPs, but is understood to comprise all blood group and platelet antigen, and preferably HPA SNPs that may be analyzed in accordance with the teachings of the present invention and using the products, protocols and methods of the present invention.

The present invention also provides the DNA primer sequences optimized for use in a multiplex PCR format.

The present invention also provides novel DNA probe sequences used to detect the SNPs of interest.

The present invention provides a method for the simultaneous detection of a plurality of blood group SNPs. More specifically, the present invention provides a method for the simultaneous detection of at least 19 blood group SNPs; RHD (2), RHC/c, RHE/e, S/s, Duffy (a/b), Kidd (a/b), Diego (a/b), Kell K1/K2, Kell K3/K4, and HPA-1a/b simultaneously. The method of the present invention provides (1) DNA sequences corresponding to the PCR primer pairs optimized for multiplex use to identify a plurality of blood group and platelet antigens simultaneously; (2) Novel DNA sequences used to identify the single nucleotide polymorphisms (SNPs) that represent underlying DNA blood group and platelet antigens; and (3) The combination of SNP analyses including blood group and platelet antigens.

To support and validate the teachings of the present invention various experimental tests have been completed and analyzed. Numerous validating experimental data has been recorded, however, for the purpose of simplicity the following example is provided. Each step in the validating experiment is noted below:

(1) Ultra high throughput (UHT) Multiplex SNP analyses on 372 unrelated blood donor specimens for RHD (2), RHC/c, RHE/e, S/s, FY1/FY2 (2), JK1/JK2, DI1/DI2, KEL1/KEL2, KEL3/KEL4, and HPA-1A/B genotypes and corresponding phenotypes was examined, and data was recorded (please refer to Appendix A for the raw data accumulated, and Table 5 for a Summary of the results obtained).

(2) Manual PCR-RFLP analyses was performed on some of the 372 specimens for some of the blood group SNPs to for comparison to the results obtained in Step (1).

(3) Serological analyses was also performed on some of the 372 specimens for each of the blood group and HPA SNPs using Health Canada regulated reagents performed by licensed medical technologists in a provincially licensed laboratory.

(4) Serological analyses was also performed on some of the 372 specimens for each of the blood group and platelet antigens by unlicensed research technologists using Health Canada regulated reagents and methodologies in an unlicensed laboratory.

The results obtained from the above validating experimental data is provided below by way of supportive Figures and Tables.

1. SNP Platform Data Generation.

The robotic platform produces fluorescence for each sample which are presented in 'scatter plots' (as illustrated in FIG. 1) for the operator to review. Sample genotype results are shown for each blood group SNP and are graphed using logarithmic and XY scatter plots (upper right). Green, orange or blue sample designations represent CC, TC and TT genotype calls respectively. No fluorescence represents an assay failure (FL) for that sample.

2. SNP Data Manipulation and Analysis.

The SNP results of a scatter plot are electronically exported to a spreadsheet and examined for total sample failure and individual SNP failure rates. Twelve SNP results for 372 DNA samples are summarized in Table 3 with sample failure rates (shown on the right) and individual SNP success rates (shown at the bottom). Three hundred and fifty seven of 372 samples (96%) had results for at least one SNP. Individual SNP results ranged from 80% to 100%; only one SNP result success rate was <98%. Individual SNP failures do not affect the results of a sample for other SNPs that do not fail.

3. SNP Allele Frequency Analysis.

The SNP results where then compared with published phenotype frequencies for Caucasians and Blacks and are summarized in Table 5 above. The data shows that the allele frequencies are consistent with the accepted published frequencies for Caucasians and Blacks.

3.1 SNP Allele Result Compared to the Serological Result.

RhD status was compared between the serological result and the SNP analysis for RHD exon 4, and 9 (RHD Exon 4, RHD Exon 9, respectively). Table 4 summarizes the comparison. 287 of 291 (98.6%) RhD positive units and 55 of 66 (83.3%) RhD negative units were identified correctly using the UHT SNP platform.

3.2 SNP Analysis compared to Manual PCR-RFLP.

Figures 3A, 3B:
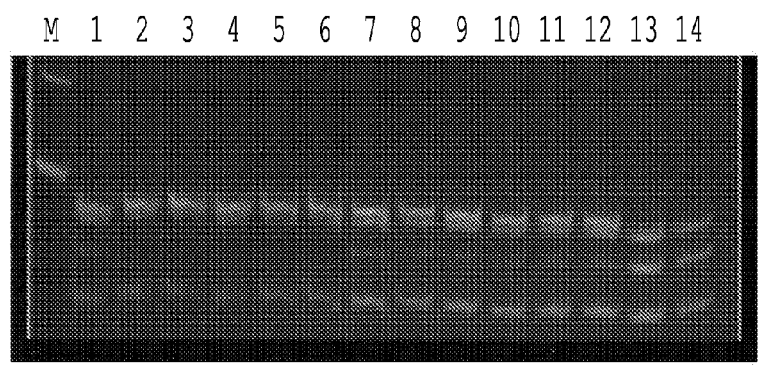
FIG. 3 Representative samples JK genotyped by manual PCR-RFLP analysis using MnlI (A) and the tabulated comparative results with the UHT SNP analysis (B).
Figure 4A:
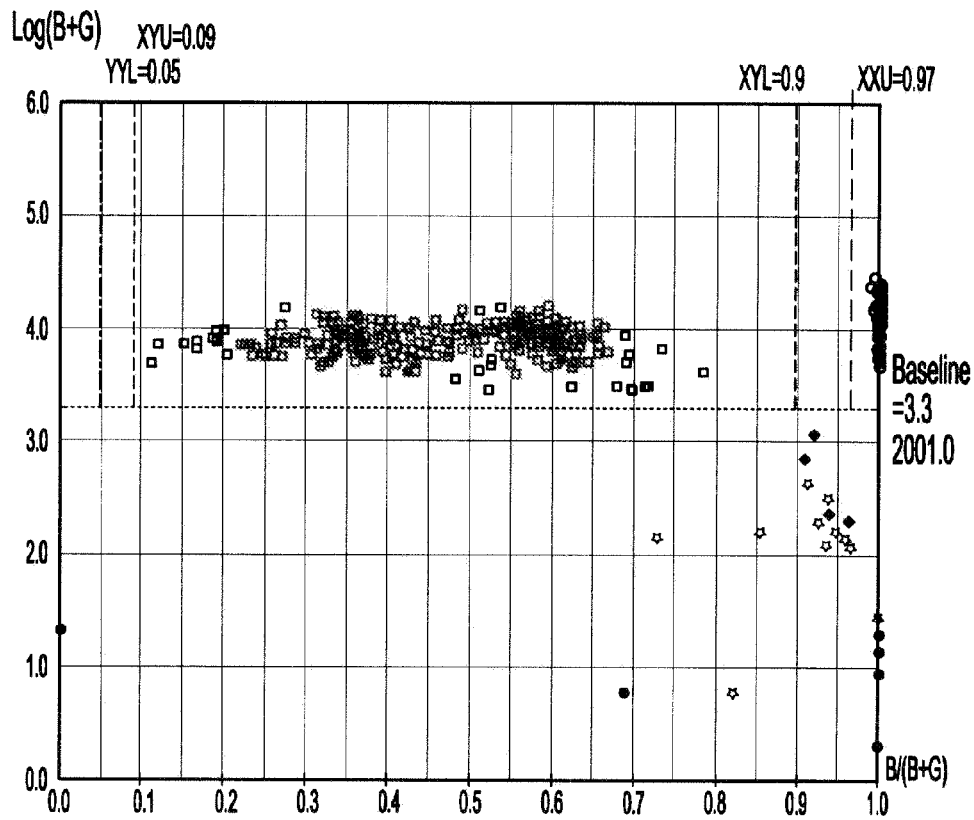
FIG. 4 A-L Computer screen displays of typical UHT SNP scatter plots to sort the fluorescence of a C/T SNP for various blood group and HPA genotypes.
Figure 4A:
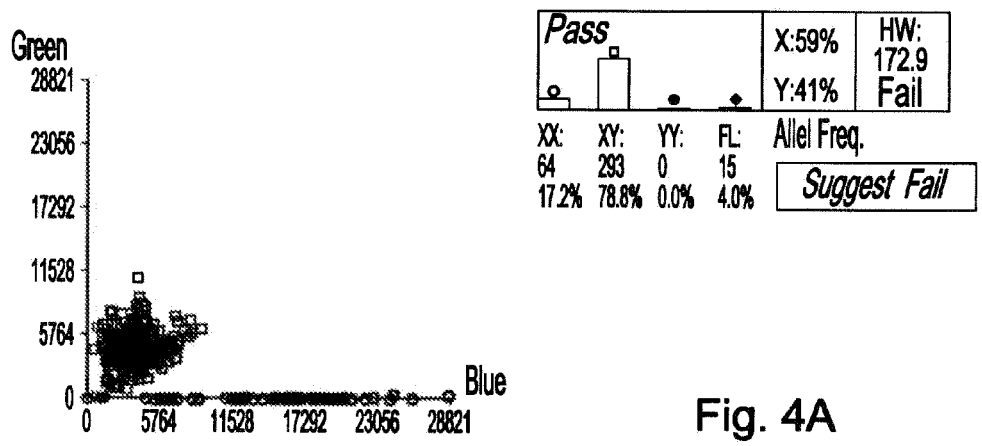
Figure 4B:
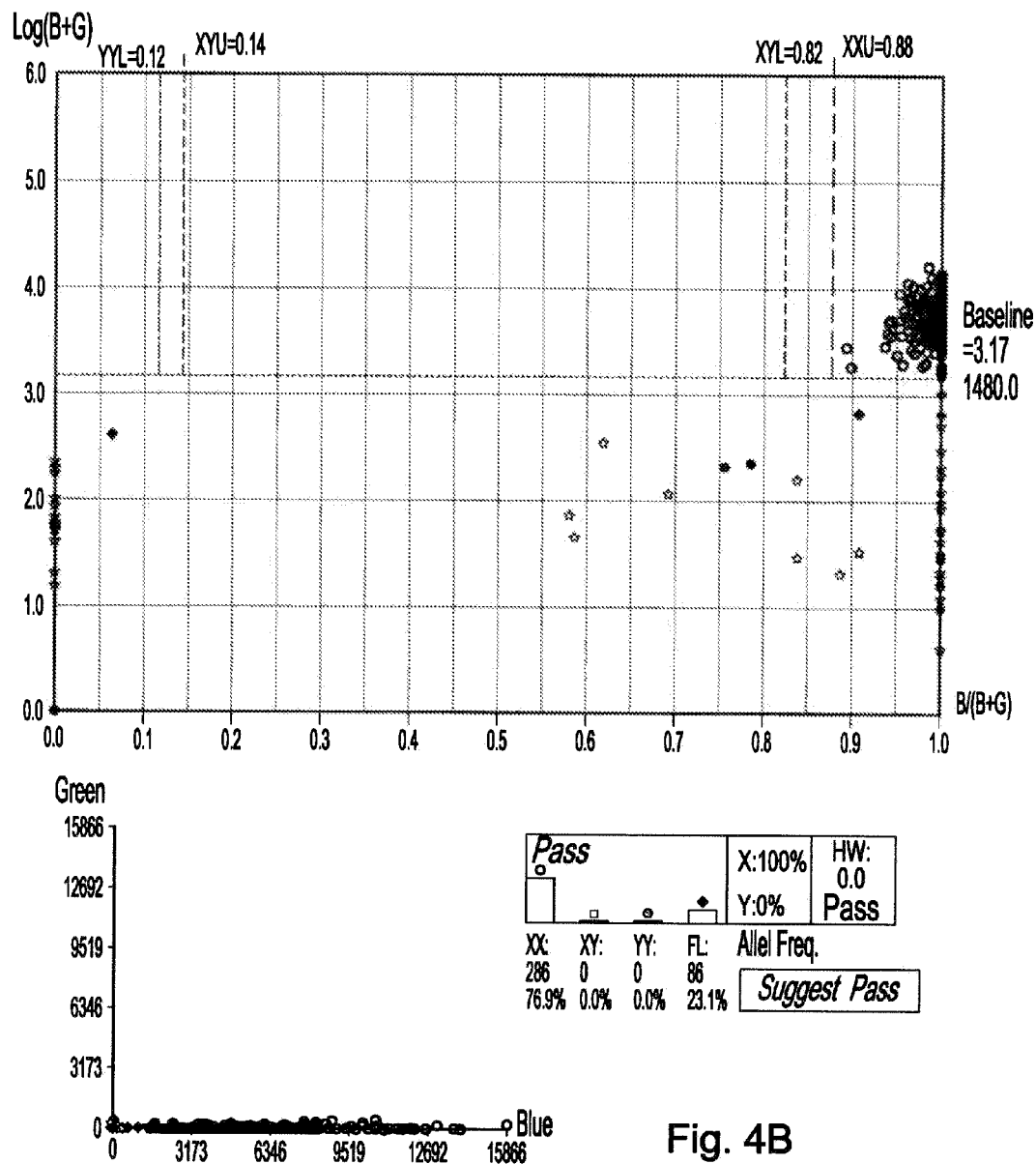
Figure 4C:
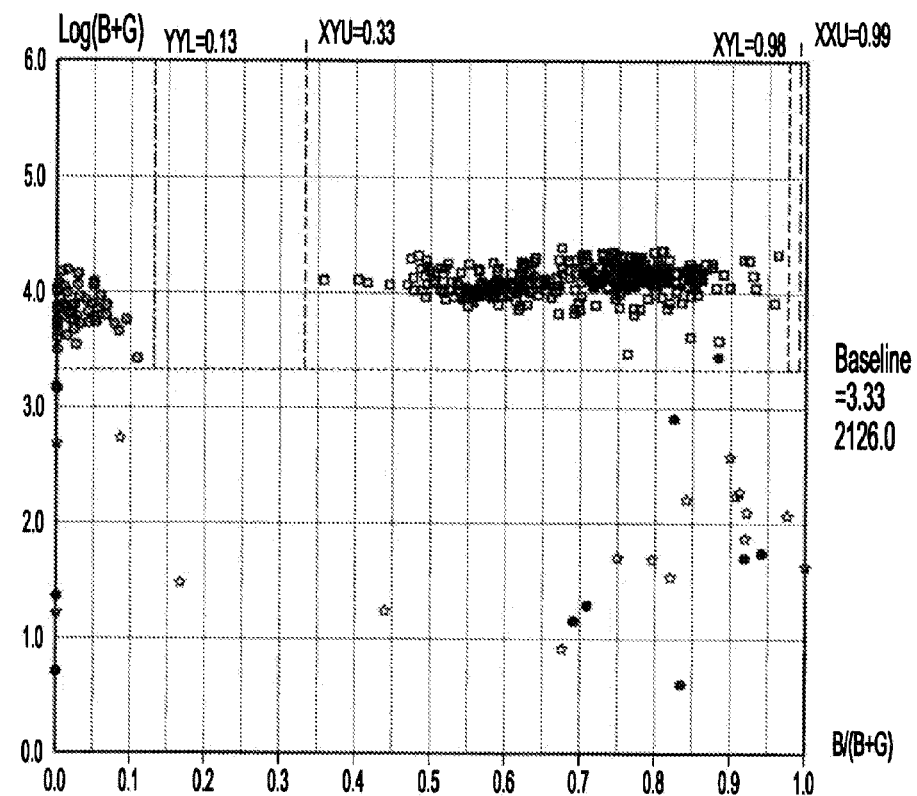
Figure 4C:
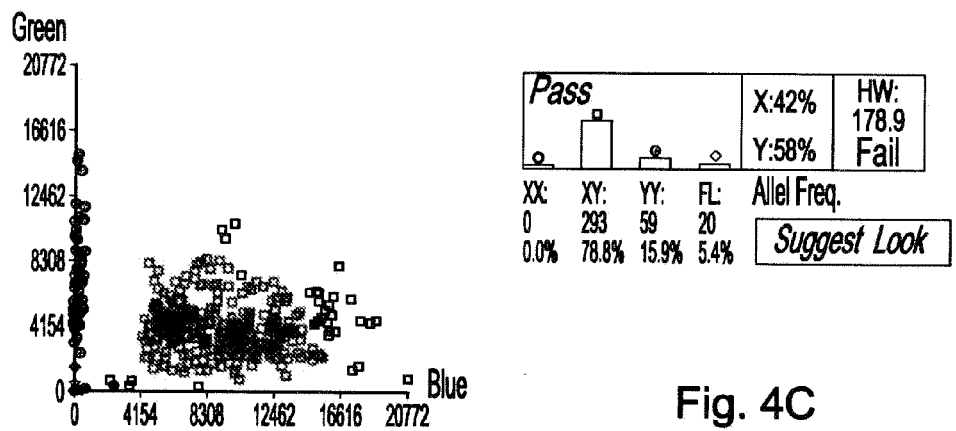
Figure 4D:
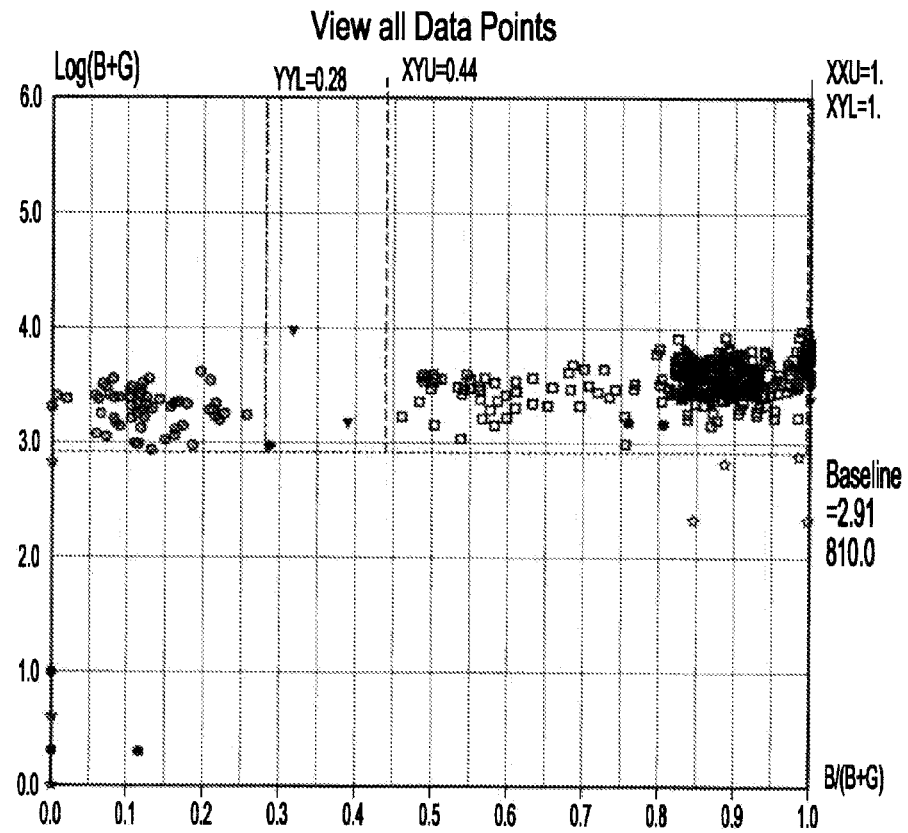
Figure 4D:
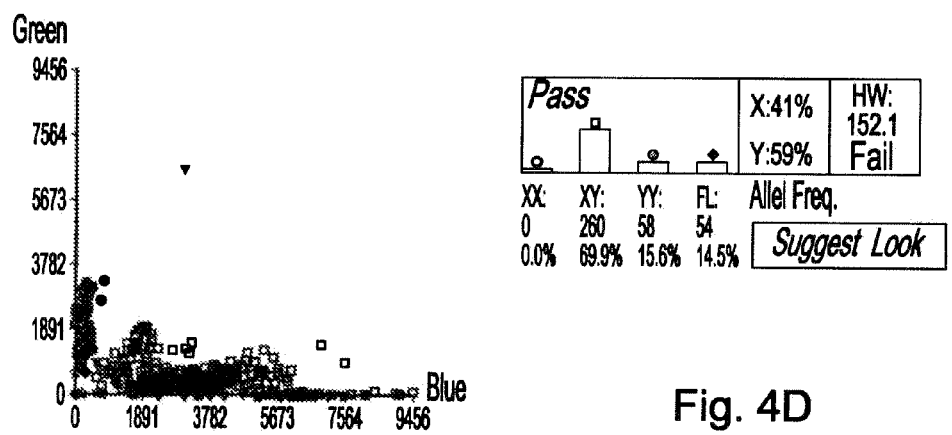
Figure 4E:
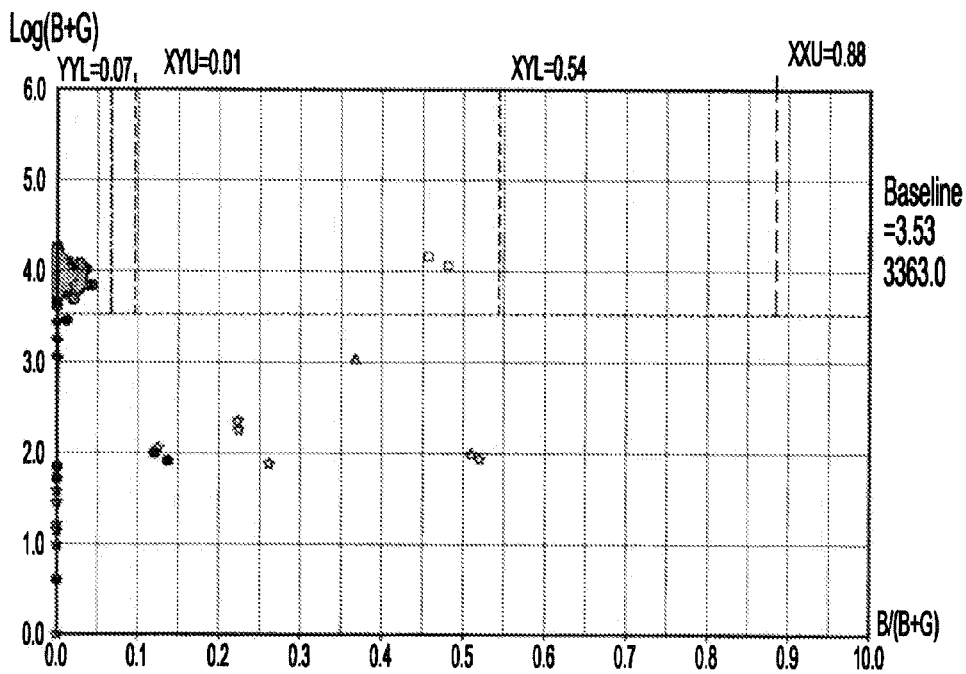
Figure 4E:
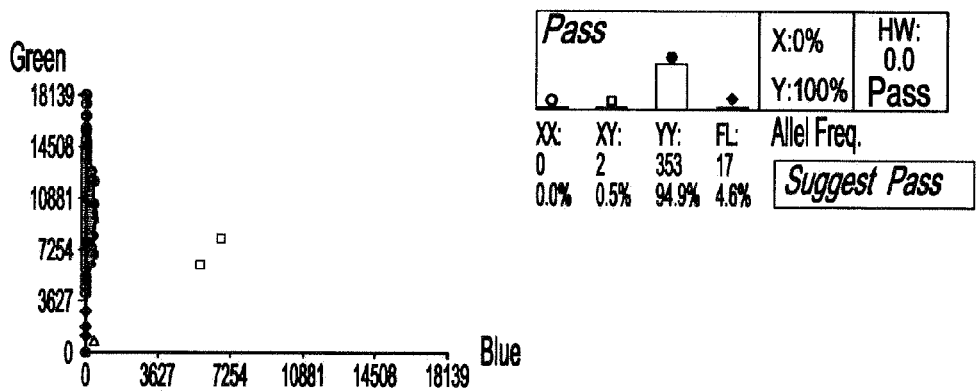
Figure 4F:
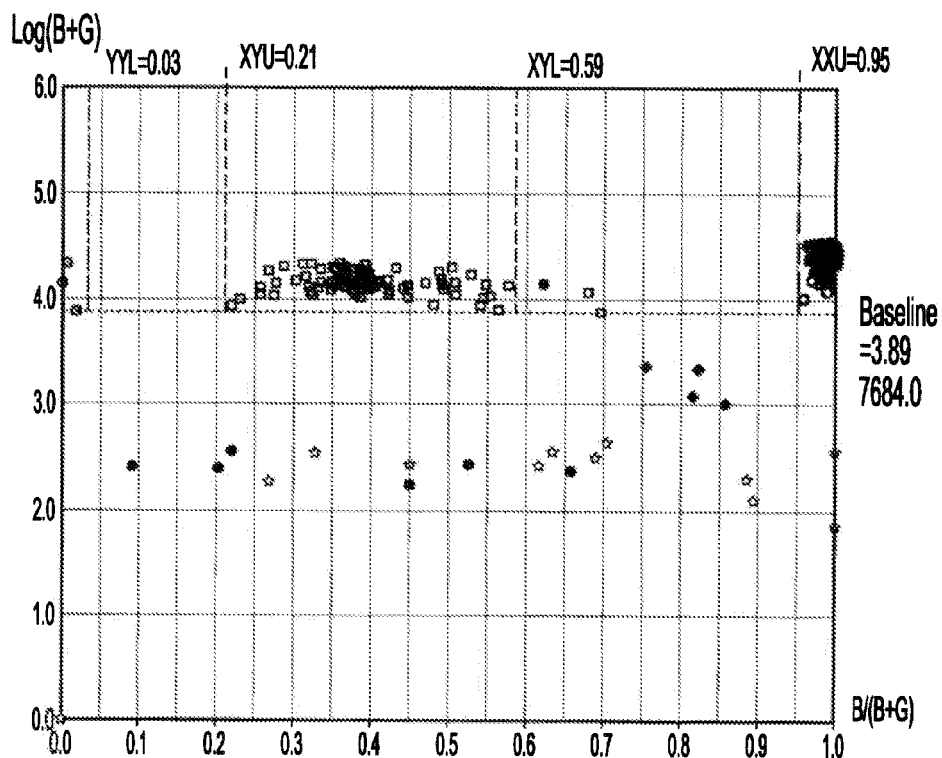
Figure 4F:
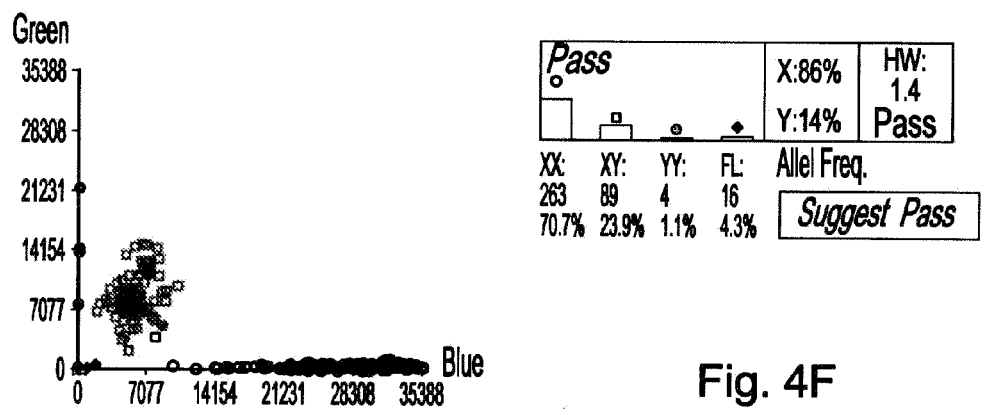
Figure 4G:
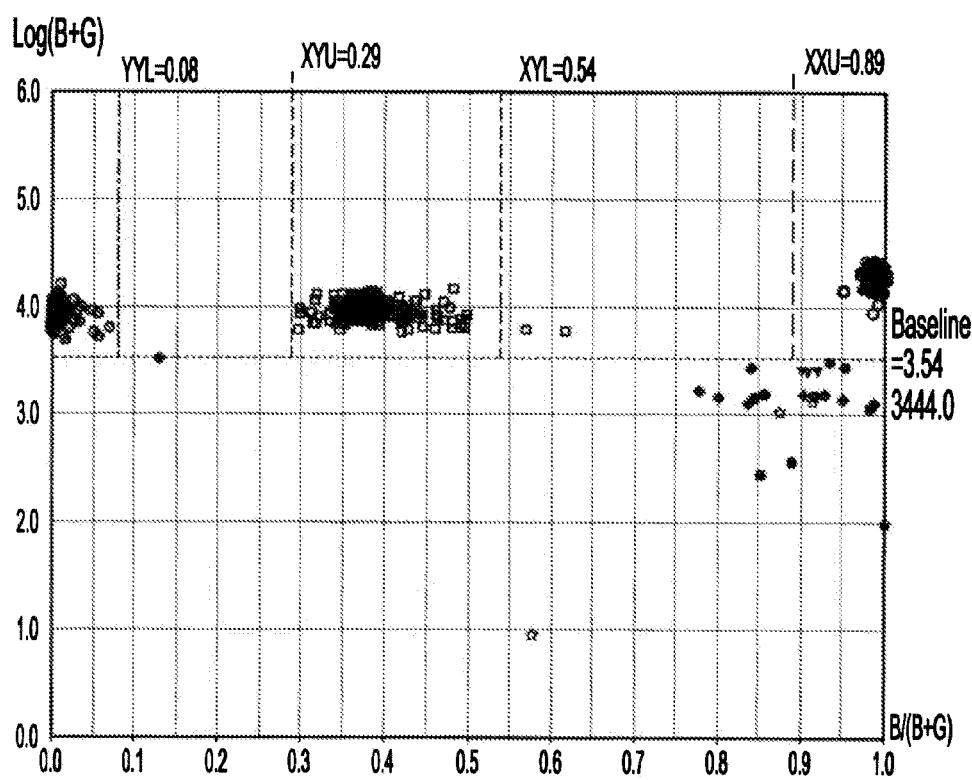
Figure 4G:
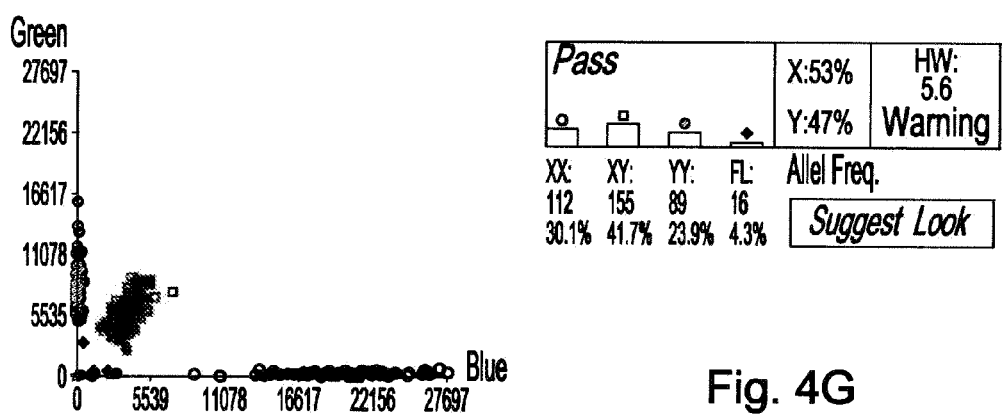
Figure 4H:
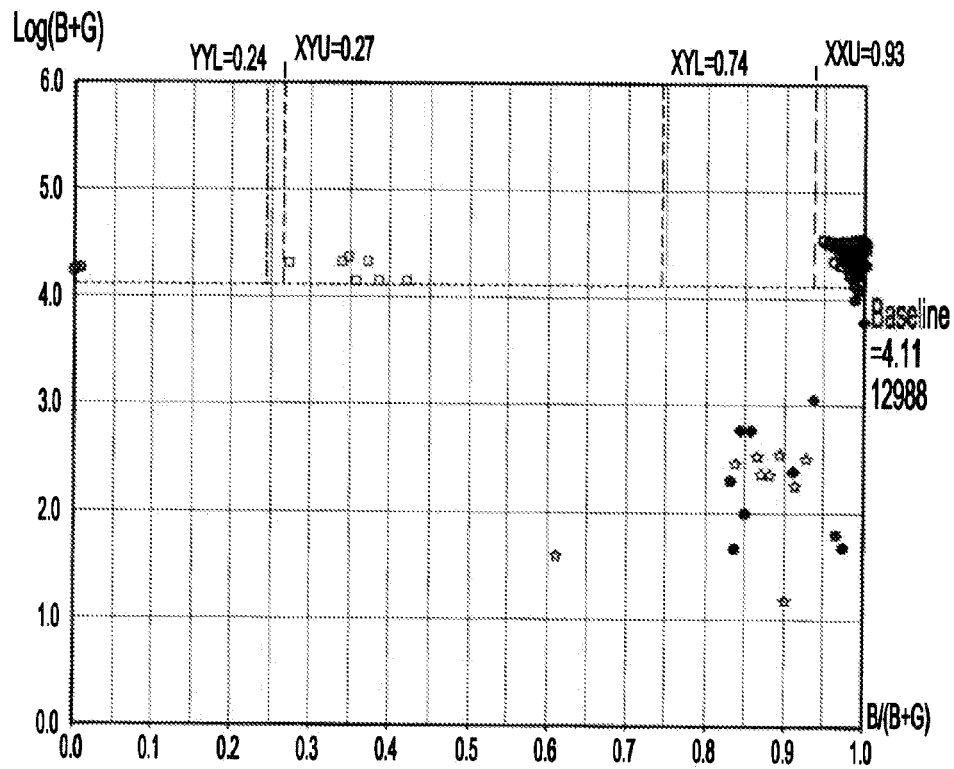
Figure 4H:
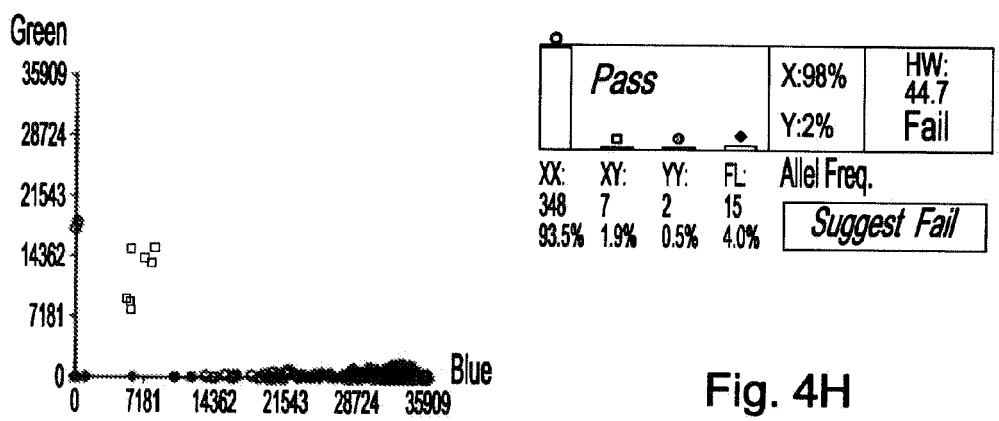
Figure 4I:
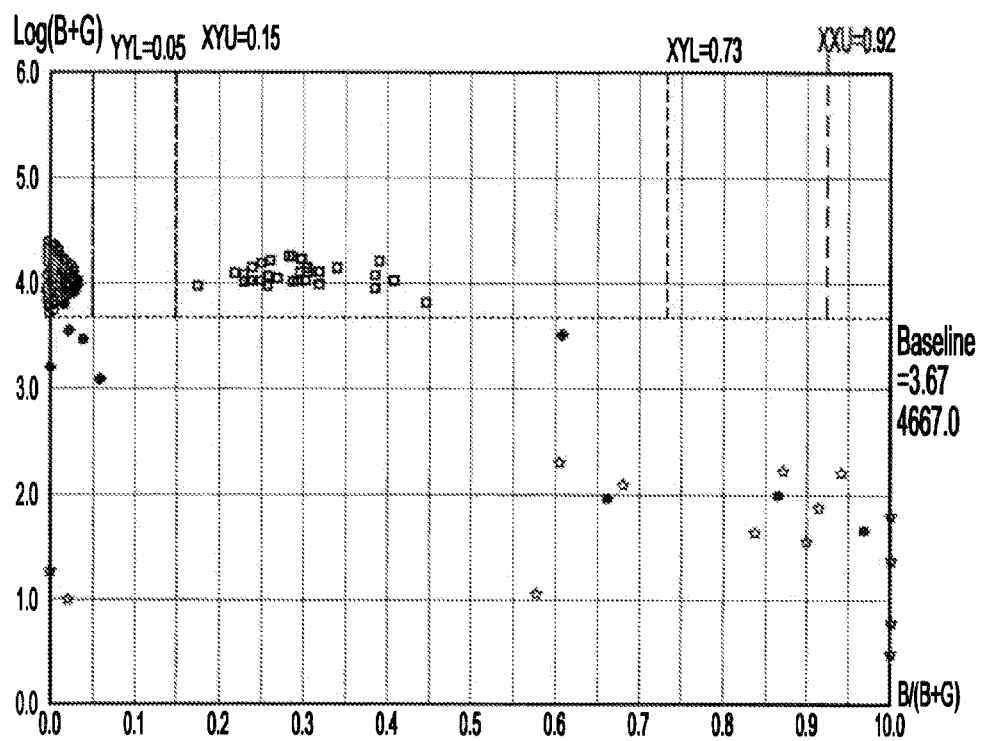
Figure 4I:
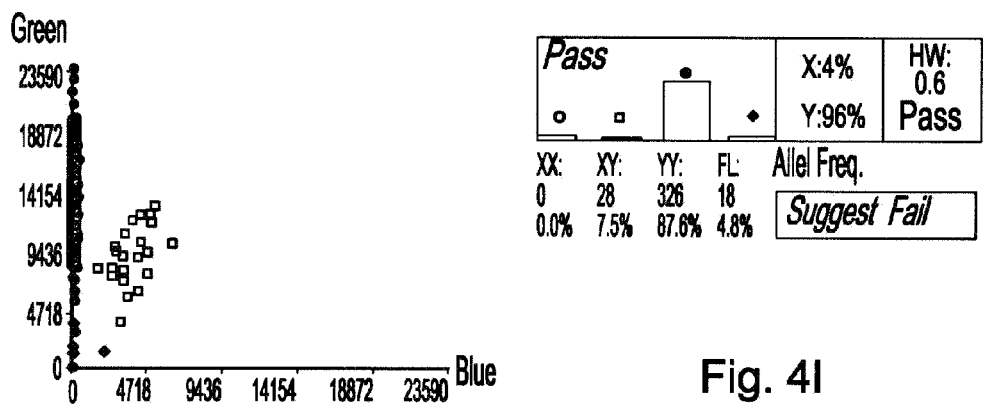
Figure 4J:
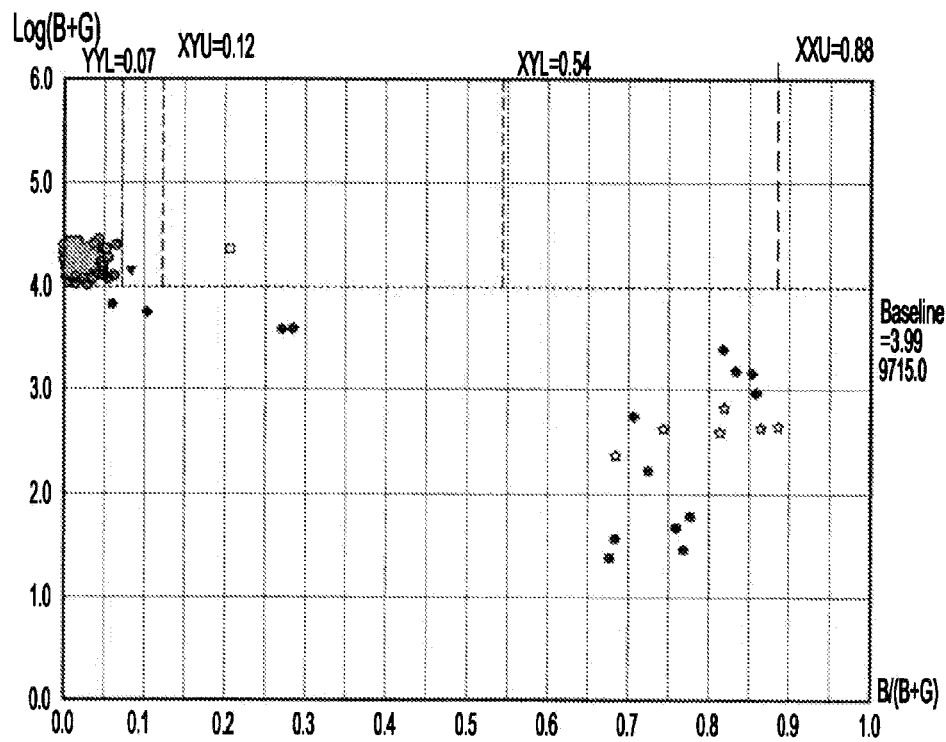
Figure 4J:
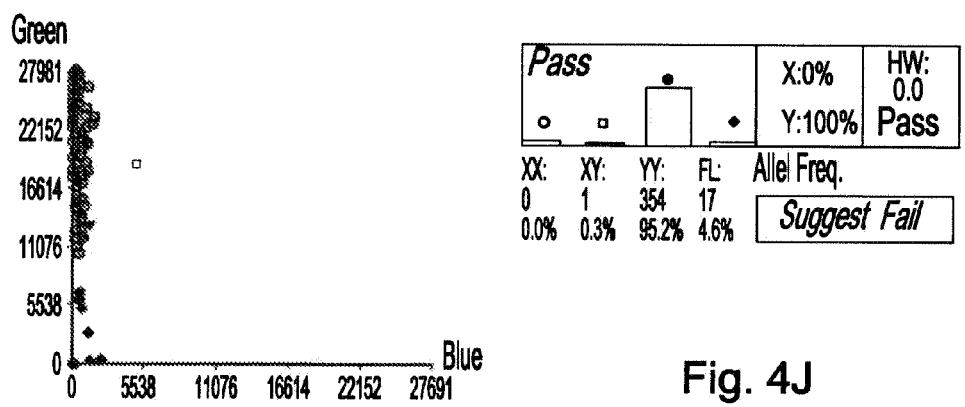
Figure 4K:
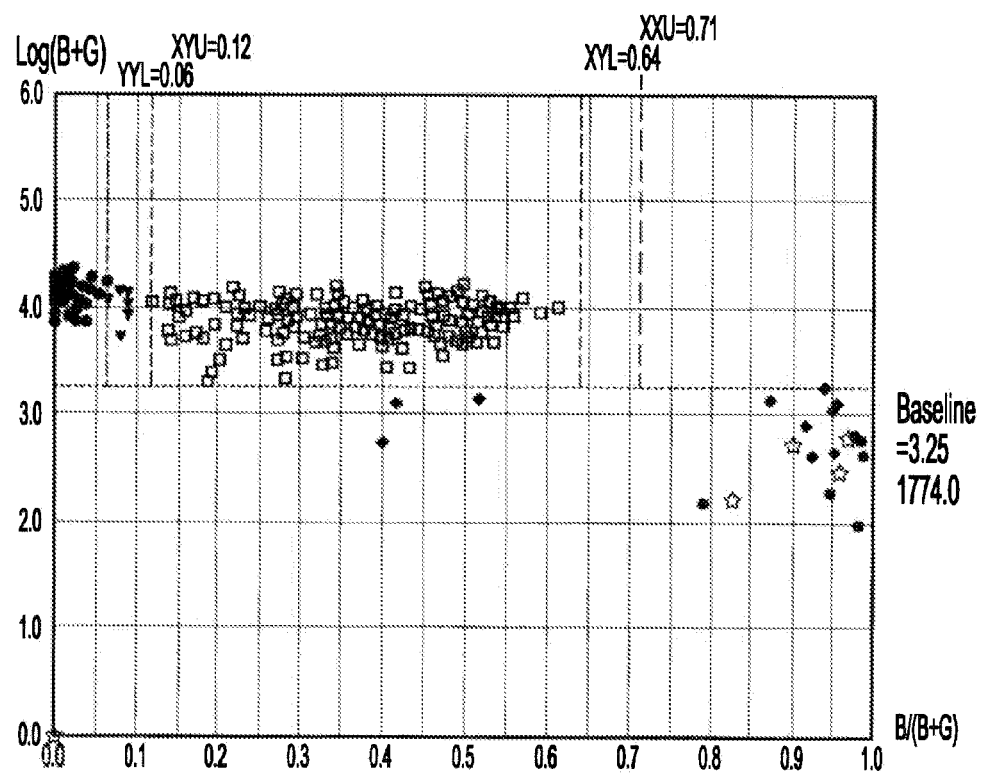
Figure 4K:
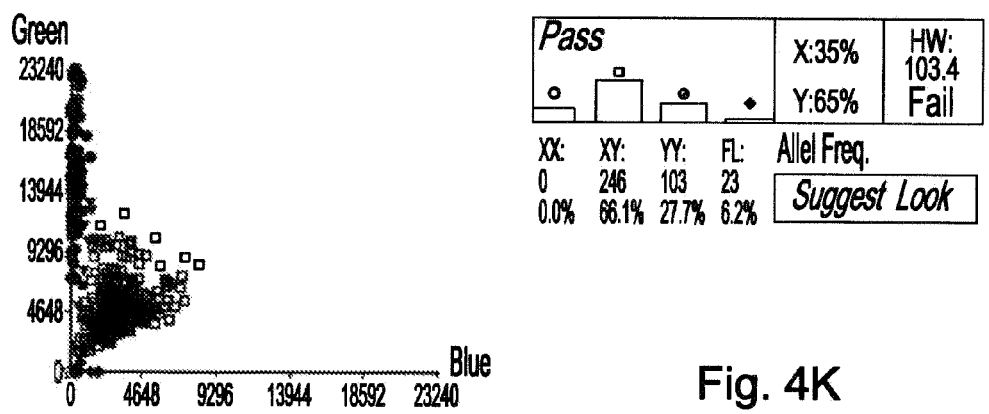
Figure 4L:
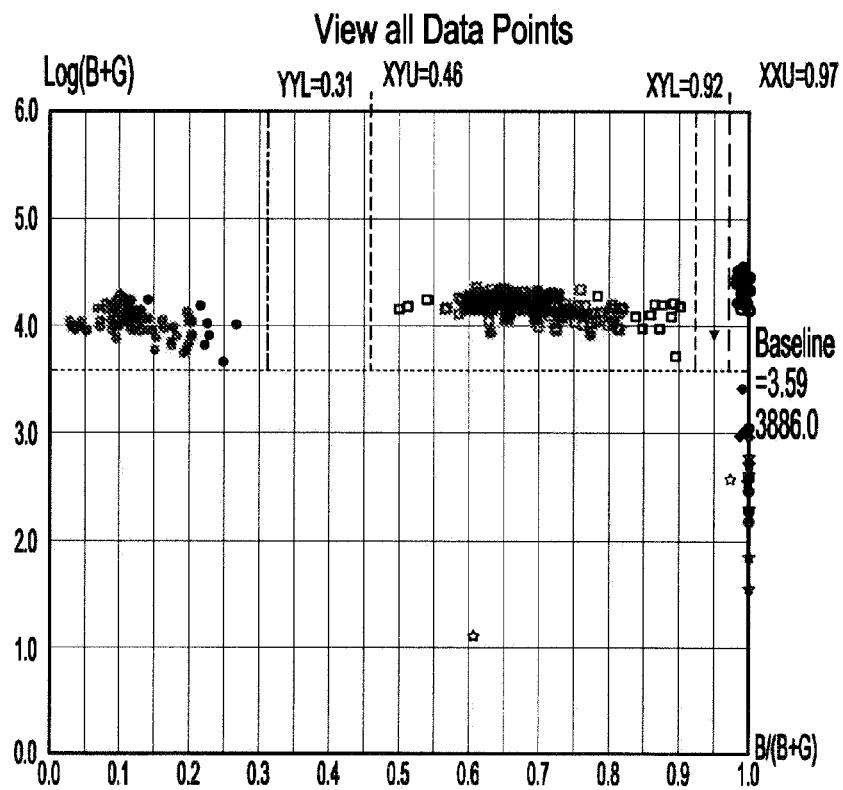
Figure 4L:
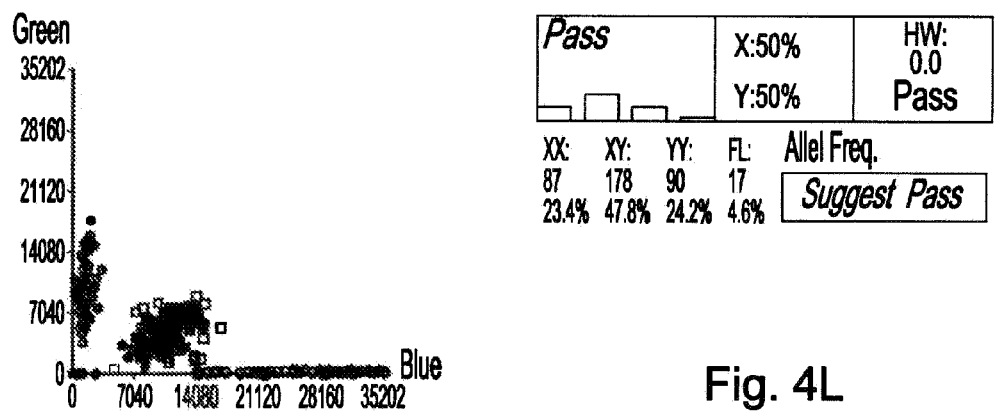

Some of the UHT SNP genotype results were compared with manual PCR-RFLP analysis performed independently. The results show 100% concordance. A representative PCR-RFLP is shown in FIG. 3.

The genotyping technology provided in the present invention queries and analyzes SNPs using single base-pair primer extension. In brief, the genomic region surrounding the SNP of interest is amplified and used as a template for the ensuing hybridization and single nucleotide extension of the SNP specific extension primer. The extension primer is designed to hybridize adjacent to the polymorphic nucleotide(s) and enables us to query bi-allelic polymorphisms, small insertions, deletions or inversions. The 5' extension primer tags are hybridized to the complementary DNA sequence on microarrayed plates and incorporation of Bidopy- and Tamra-labeled ddNTPs are detected by laser-microplate fluorescence for each individual blood group and HPA SNP. Individual sample genotypes are generated through automated imaging and analysis software as shown in the genotype scatter plots of FIG. 1.

The embodiment(s) of the invention described above is (are) intended to be exemplary only. The scope of the invention is therefore intended to be limited solely by the scope of the appended claims.

What is claimed is:

1. A probe consisting of a nucleotide sequence as set forth in SEQ ID NO: 26.

2. A blood group/platelet antigen typing kit comprising a first oligonucleotide consisting of a nucleotide sequence as set forth in SEQ ID NO: 3, a second oligonucleotide consisting of a nucleotide sequence as set forth in SEQ ID NO: 4 and a probe consisting of a nucleotide sequence as set forth in SEQ ID NO: 26.

3. A method of detecting a blood group or platelet antigen in a sample, said method comprising:
   (a) providing genomic DNA from said sample;
   (b) submitting the genomic DNA of step (a) to a PCR amplification with at least one pair of oligonucleotides to obtain at least one amplification product, said at least one pair of oligonucleotides comprising a first oligonculeotide and a second oligonculeotide, said first oligonucleotide consisting of a nucleotide sequence as set forth in SEQ ID NO: 3 and said second oligonucleotide consisting of a nucleotide sequence as set forth in SEQ ID NO: 4; and
   (c) analyzing the at least one amplification product to detect the blood group or platelet antigen in the sample.

4. The method of claim 3, wherein the amplification product is digested with a restriction enzyme.

5. The method of claim 4, wherein said restriction enzyme is Exonuclease I or shrimp alkaline phosphatase.

6. The method of claim 3, wherein, in step (c), a nucleic acid probe consisting of the nucleotide sequence set forth between positions 21 to 45 of SEQ ID NO: 36 is used with the amplification product in a single-base pair primer extension assay to generate an extension product.

7. The method of claim 6, wherein the extension product is hybridized.

8. The method of claim 7, wherein said extension product is hybridized to a tag-arrayed microplate.

9. The method of claim 3, wherein the blood group or platelet antigen is RHD Exon 9 A/G.

* * * * *